(12) United States Patent
Oko et al.

(10) Patent No.: US 9,486,189 B2
(45) Date of Patent: Nov. 8, 2016

(54) ASSEMBLY FOR USE WITH SURGERY SYSTEM

(71) Applicants: Thomas P. Oko, Shelton, CT (US); Jason K. Blake, Orange, CT (US)

(72) Inventors: Thomas P. Oko, Shelton, CT (US); Jason K. Blake, Orange, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 869 days.

(21) Appl. No.: 13/622,484

(22) Filed: Sep. 19, 2012

(65) Prior Publication Data

US 2013/0018388 A1 Jan. 17, 2013

Related U.S. Application Data

(63) Continuation-in-part of application No. 12/958,953, filed on Dec. 2, 2010, and a continuation-in-part of application No. PCT/US2011/063082, filed on Dec. 2, 2011.

(51) Int. Cl.
| | |
|---|---|
| *A61B 17/00* | (2006.01) |
| *A61B 17/062* | (2006.01) |
| *A61B 17/068* | (2006.01) |
| *A61B 17/08* | (2006.01) |
| *A61B 17/10* | (2006.01) |

(52) U.S. Cl.
CPC ........ *A61B 17/00234* (2013.01); *A61B 17/062* (2013.01); *A61B 17/068* (2013.01); *A61B 17/08* (2013.01); *A61B 17/10* (2013.01); *A61B 34/30* (2016.02); *A61B 2017/00477* (2013.01); *A61B 2090/3784* (2016.02)

(58) Field of Classification Search
CPC ...... A61B 17/00; A61B 17/70; A61B 17/62; A61B 18/04; A61B 17/04; A61F 2/68
USPC .................................. 606/80, 278, 308, 164
See application file for complete search history.

(56) References Cited

U.S. PATENT DOCUMENTS

| | | |
|---|---|---|
| 5,013,304 A | 5/1991 | Russell et al. |
| 5,078,140 A | 1/1992 | Kwoh |
| 5,515,853 A | 5/1996 | Smith et al. |

(Continued)

OTHER PUBLICATIONS

Satava, Ho the Future of Surgery is Changing: Robotics, Telesurgery, Surgical Simulators and Other Advanced Technologies, Jurnalul de Chirurgie, Iasi, 2009, vol. 5, Nr. 4, pp. 311-325.

(Continued)

*Primary Examiner* — William Thomson
*Assistant Examiner* — Victor Shapiro
(74) *Attorney, Agent, or Firm* — McCarter & English, LLP

(57) ABSTRACT

The present disclosure provides systems, assemblies and methods for surgery (e.g., robotic surgery). More particularly, the present disclosure provides systems and methods for releasably securing or attaching an assembly for use in a surgical procedure with respect to a user-operable surgical device. In general, the present disclosure provides systems and methods for releasably securing or attaching an assembly with respect to and for use with a user-operable surgery system. Systems and methods for releasably securing or attaching an assembly (e.g., imaging/surgical assembly) having a receiver member with respect to a user-operable grasper member of a surgery system are provided. The receiver member may be releasably and/or detachably securable to the surgical/imaging assembly.

30 Claims, 21 Drawing Sheets

(56) References Cited

U.S. PATENT DOCUMENTS

| | | | |
|---|---|---|---|
| 5,624,441 A * | 4/1997 | Sherman et al. | 606/278 |
| 5,704,914 A * | 1/1998 | Stocking et al. | 604/164.07 |
| 5,792,135 A | 8/1998 | Madhani et al. | |
| 5,797,849 A | 8/1998 | Vesely et al. | |
| 5,797,900 A | 8/1998 | Madhani et al. | |
| 5,807,377 A | 9/1998 | Madhani et al. | |
| 5,808,665 A | 9/1998 | Green | |
| 5,857,964 A | 1/1999 | Konstrum et al. | |
| 5,876,325 A | 3/1999 | Mizuno et al. | |
| 6,197,017 B1 | 3/2001 | Brock et al. | |
| 6,206,903 B1 | 3/2001 | Ramans | |
| 6,246,200 B1 | 6/2001 | Blumenkranz et al. | |
| 6,246,898 B1 | 6/2001 | Vesely et al. | |
| 6,309,397 B1 | 10/2001 | Julian et al. | |
| 6,322,567 B1 | 11/2001 | Mittelstadt et al. | |
| 6,371,952 B1 | 4/2002 | Madhani et al. | |
| 6,394,998 B1 | 5/2002 | Wallace et al. | |
| 6,398,726 B1 | 6/2002 | Ramans et al. | |
| 6,424,885 B1 | 7/2002 | Niemeyer et al. | |
| 6,425,865 B1 | 7/2002 | Salcudean et al. | |
| 6,432,112 B2 | 8/2002 | Brock et al. | |
| 6,441,577 B2 | 8/2002 | Blumenkranz et al. | |
| 6,451,027 B1 | 9/2002 | Cooper et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,522,906 B1 | 2/2003 | Salisbury et al. | |
| 6,547,789 B1 * | 4/2003 | Ventre et al. | 606/308 |
| 6,554,790 B1 | 4/2003 | Moll | |
| 6,587,750 B2 | 7/2003 | Gerbi et al. | |
| 6,607,533 B2 * | 8/2003 | Del Rio et al. | 606/80 |
| 6,620,173 B2 | 9/2003 | Berbi et al. | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,692,485 B1 | 2/2004 | Brock et al. | |
| 6,714,839 B2 | 3/2004 | Salisbury et al. | |
| 6,720,988 B1 | 4/2004 | Gere et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,782,285 B2 | 8/2004 | Birkenbach et al. | |
| 6,783,524 B2 | 8/2004 | Anderson et al. | |
| 6,799,065 B1 | 9/2004 | Niemeyer | |
| 6,817,975 B1 | 11/2004 | Farr et al. | |
| 6,840,938 B1 | 1/2005 | Morley et al. | |
| 6,858,003 B2 | 2/2005 | Evans et al. | |
| 6,902,560 B1 | 6/2005 | Morley et al. | |
| 6,905,460 B2 | 6/2005 | Wang et al. | |
| 6,936,042 B2 | 8/2005 | Wallace et al. | |
| 6,979,423 B2 | 12/2005 | Moll | |
| 6,991,627 B2 | 1/2006 | Madhani et al. | |
| 6,994,703 B2 | 2/2006 | Wang et al. | |
| 6,994,708 B2 | 2/2006 | Manzo | |
| 7,025,064 B2 | 4/2006 | Wang et al. | |
| 7,027,892 B2 | 4/2006 | Wang et al. | |
| 7,074,179 B2 | 7/2006 | Wang et al. | |
| 7,076,286 B2 | 7/2006 | Mizoguchi et al. | |
| 7,083,615 B2 | 8/2006 | Peterson et al. | |
| 7,087,049 B2 | 8/2006 | Nowlin et al. | |
| 7,090,683 B2 | 8/2006 | Brock et al. | |
| 7,097,640 B2 | 8/2006 | Wang et al. | |
| 7,107,090 B2 | 9/2006 | Salisbury et al. | |
| 7,125,403 B2 | 10/2006 | Julian et al. | |
| 7,155,315 B2 | 12/2006 | Niemeyer et al. | |
| 7,155,316 B2 | 12/2006 | Sutherland et al. | |
| 7,206,626 B2 | 4/2007 | Quaid et al. | |
| 7,206,627 B2 | 4/2007 | Abovitz et al. | |
| 7,214,230 B2 | 5/2007 | Brock et al. | |
| 7,217,240 B2 | 5/2007 | Snow | |
| 7,250,028 B2 | 7/2007 | Julian et al. | |
| 7,276,065 B2 | 10/2007 | Morley et al. | |
| 7,277,120 B2 | 10/2007 | Gere et al. | |
| 7,294,106 B2 | 11/2007 | Birkenbach et al. | |
| 7,306,597 B2 | 12/2007 | Manzo | |
| 7,313,430 B2 | 12/2007 | Urquhart et al. | |
| 7,316,681 B2 | 1/2008 | Madhani et al. | |
| 7,357,774 B2 | 4/2008 | Cooper | |
| 7,367,973 B2 | 5/2008 | Manzo et al. | |
| 7,371,210 B2 | 5/2008 | Brock et al. | |
| 7,386,365 B2 | 6/2008 | Nixon | |
| 7,387,126 B2 | 6/2008 | Cox et al. | |
| 7,390,325 B2 | 6/2008 | Wang et al. | |
| 7,395,249 B2 | 7/2008 | Wang et al. | |
| 7,398,707 B2 | 7/2008 | Morley et al. | |
| 7,413,565 B2 | 8/2008 | Wang et al. | |
| 7,440,793 B2 | 10/2008 | Chauhan et al. | |
| 7,507,199 B2 | 3/2009 | Wang et al. | |
| 7,524,320 B2 | 4/2009 | Tierney et al. | |
| 7,543,588 B2 | 6/2009 | Wang et al. | |
| 7,559,891 B2 | 7/2009 | Farr et al. | |
| 7,567,834 B2 | 7/2009 | Clayton et al. | |
| 7,574,250 B2 | 8/2009 | Niemeyer | |
| 7,660,623 B2 | 2/2010 | Hunter et al. | |
| 7,677,129 B2 | 3/2010 | Schena et al. | |
| 7,682,357 B2 | 3/2010 | Ghodoussi et al. | |
| 7,689,320 B2 | 3/2010 | Prisco et al. | |
| 7,691,098 B2 | 4/2010 | Wallace et al. | |
| 7,695,481 B2 | 4/2010 | Wang et al. | |
| 7,713,205 B2 | 5/2010 | Fu et al. | |
| 7,713,210 B2 | 5/2010 | Byrd et al. | |
| 7,722,599 B2 | 5/2010 | Julian et al. | |
| 7,725,214 B2 | 5/2010 | Diolati | |
| 7,741,802 B2 | 6/2010 | Prisco et al. | |
| 7,763,015 B2 | 7/2010 | Cooper et al. | |
| 7,778,733 B2 | 8/2010 | Nowlin et al. | |
| 7,780,651 B2 | 8/2010 | Madhani et al. | |
| 7,785,320 B2 | 8/2010 | Wang et al. | |
| 7,806,891 B2 | 10/2010 | Nowlin et al. | |
| 2002/0042620 A1 | 4/2002 | Julian et al. | |
| 2002/0082498 A1 | 6/2002 | Wendt et al. | |
| 2002/0103476 A1 | 8/2002 | Madhani et al. | |
| 2002/0111621 A1 | 8/2002 | Wallace et al. | |
| 2002/0120254 A1 | 8/2002 | Julian et al. | |
| 2002/0128552 A1 | 9/2002 | Nowlin et al. | |
| 2003/0109877 A1 | 6/2003 | Morley et al. | |
| 2003/0181800 A1 | 9/2003 | Bonutti | |
| 2003/0216715 A1 | 11/2003 | Moll et al. | |
| 2004/0039485 A1 | 2/2004 | Niemeyer et al. | |
| 2004/0077939 A1 | 4/2004 | Graumann | |
| 2004/0152972 A1 | 8/2004 | Hunter | |
| 2005/0021018 A1 | 1/2005 | Anderson et al. | |
| 2005/0027397 A1 | 2/2005 | Niemeyer | |
| 2005/0043718 A1 | 2/2005 | Madhani et al. | |
| 2005/0090809 A1 | 4/2005 | Cooper et al. | |
| 2005/0096502 A1 | 5/2005 | Khalili | |
| 2005/0119638 A1 | 6/2005 | Jensen | |
| 2005/0187473 A1 | 8/2005 | Boctor et al. | |
| 2005/0203410 A1 | 9/2005 | Jenkins | |
| 2005/0234433 A1 | 10/2005 | Wang et al. | |
| 2005/0261591 A1 | 11/2005 | Boctor et al. | |
| 2006/0074406 A1 | 4/2006 | Cooper et al. | |
| 2006/0074415 A1 | 4/2006 | Scott et al. | |
| 2006/0079884 A1 | 4/2006 | Manzo et al. | |
| 2006/0142657 A1 | 6/2006 | Quaid et al. | |
| 2006/0149418 A1 | 7/2006 | Anvari | |
| 2006/0161136 A1 | 7/2006 | Anderson et al. | |
| 2006/0167441 A1 | 7/2006 | Wang et al. | |
| 2006/0178559 A1 | 8/2006 | Kumar et al. | |
| 2006/0199999 A1 | 9/2006 | Ikeda et al. | |
| 2006/0258938 A1 | 11/2006 | Hoffman et al. | |
| 2006/0270934 A1 | 11/2006 | Savord et al. | |
| 2007/0021738 A1 | 1/2007 | Hasser et al. | |
| 2007/0032906 A1 | 2/2007 | Sutherland et al. | |
| 2007/0038080 A1 | 2/2007 | Salisbury, Jr. et al. | |
| 2007/0055144 A1 | 3/2007 | Neustadter et al. | |
| 2007/0156017 A1 | 7/2007 | Lamprecht et al. | |
| 2007/0185485 A1 | 8/2007 | Hauck et al. | |
| 2007/0198008 A1 | 8/2007 | Hauck et al. | |
| 2007/0208223 A1 | 9/2007 | Julian et al. | |
| 2007/0283970 A1 | 12/2007 | Mohr et al. | |

(56) References Cited

U.S. PATENT DOCUMENTS

| | | |
|---|---|---|
| 2007/0285508 A1 | 12/2007 | Gere et al. |
| 2007/0287884 A1 | 12/2007 | Schena |
| 2007/0287889 A1 | 12/2007 | Mohr |
| 2008/0004603 A1 | 1/2008 | Larkin et al. |
| 2008/0004632 A1 | 1/2008 | Sutherland et al. |
| 2008/0004633 A1 | 1/2008 | Arata et al. |
| 2008/0027464 A1 | 1/2008 | Moll et al. |
| 2008/0033240 A1 | 2/2008 | Hoffman et al. |
| 2008/0058836 A1 | 3/2008 | Moll et al. |
| 2008/0058861 A1 | 3/2008 | Cooper et al. |
| 2008/0064921 A1 | 3/2008 | Larkin et al. |
| 2008/0065098 A1 | 3/2008 | Larkin |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065109 A1 | 3/2008 | Larkin |
| 2008/0071289 A1 | 3/2008 | Cooper et al. |
| 2008/0071291 A1 | 3/2008 | Duval et al. |
| 2008/0077158 A1 | 3/2008 | Haider et al. |
| 2008/0082109 A1 | 4/2008 | Moll et al. |
| 2008/0091244 A1 | 4/2008 | Richardson |
| 2008/0103492 A1 | 5/2008 | Morley et al. |
| 2008/0119714 A1 | 5/2008 | Meissner et al. |
| 2008/0119727 A1 | 5/2008 | Barbagli et al. |
| 2008/0140087 A1 | 6/2008 | Barbagli |
| 2008/0151041 A1 | 6/2008 | Shafer et al. |
| 2008/0161677 A1 | 7/2008 | Sutherland et al. |
| 2008/0161830 A1 | 7/2008 | Sutherland et al. |
| 2008/0167545 A1 | 7/2008 | Meissner et al. |
| 2008/0167750 A1 | 7/2008 | Stahler et al. |
| 2008/0177279 A1 | 7/2008 | Sumanaweera et al. |
| 2008/0186378 A1 | 8/2008 | Shen et al. |
| 2008/0200806 A1 | 8/2008 | Liu et al. |
| 2008/0221590 A1 | 9/2008 | Ikeda et al. |
| 2008/0228296 A1 | 9/2008 | Eilam et al. |
| 2008/0243064 A1 | 10/2008 | Stahler et al. |
| 2008/0243141 A1 | 10/2008 | Privitera et al. |
| 2008/0249536 A1 | 10/2008 | Stahler et al. |
| 2008/0255505 A1 | 10/2008 | Carlson et al. |
| 2008/0262480 A1 | 10/2008 | Stahler et al. |
| 2008/0262513 A1 | 10/2008 | Stahler et al. |
| 2008/0269777 A1 | 10/2008 | Appendrodt et al. |
| 2008/0294115 A1 | 11/2008 | Chen |
| 2008/0306384 A1 | 12/2008 | Boctor et al. |
| 2008/0312668 A1 | 12/2008 | Grace |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |
| 2009/0036900 A1 | 2/2009 | Moll |
| 2009/0036902 A1 | 2/2009 | DiMaio et al. |
| 2009/0062813 A1 | 3/2009 | Prisco et al. |
| 2009/0065106 A1 | 3/2009 | Kimura et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0138025 A1 | 5/2009 | Stahler et al. |
| 2009/0171332 A1 | 7/2009 | Bonneau |
| 2009/0171371 A1 | 7/2009 | Nixon et al. |
| 2009/0171372 A1 | 7/2009 | Mohr |
| 2009/0171373 A1 | 7/2009 | Farritor et al. |
| 2009/0182226 A1 | 7/2009 | Weitzner et al. |
| 2009/0192519 A1 | 7/2009 | Omori |
| 2009/0192524 A1 | 7/2009 | Itkowitz et al. |
| 2009/0234371 A1 | 9/2009 | Tierney et al. |
| 2009/0245600 A1 | 10/2009 | Hoffman et al. |
| 2009/0248036 A1 | 10/2009 | Hoffman et al. |
| 2009/0248037 A1 | 10/2009 | Prisco |
| 2009/0248040 A1 | 10/2009 | Cooper et al. |
| 2009/0248041 A1 | 10/2009 | Williams et al. |
| 2009/0248043 A1 | 10/2009 | Tierney et al. |
| 2009/0264899 A1 | 10/2009 | Appenrodt et al. |
| 2009/0268010 A1 | 10/2009 | Zhao et al. |
| 2009/0268011 A1 | 10/2009 | Scott et al. |
| 2009/0268012 A1 | 10/2009 | Scott et al. |
| 2009/0268015 A1 | 10/2009 | Scott et al. |
| 2009/0270678 A1 | 10/2009 | Scott et al. |
| 2009/0270683 A1 | 10/2009 | Farr et al. |
| 2009/0287223 A1 | 11/2009 | Pua et al. |
| 2009/0292299 A1 | 11/2009 | Cooper et al. |
| 2009/0292309 A1 | 11/2009 | Maschke |
| 2009/0299343 A1 | 12/2009 | Rogers |
| 2009/0326318 A1 | 12/2009 | Tognaccini et al. |
| 2009/0326322 A1 | 12/2009 | Diolaiti |
| 2009/0326530 A1 | 12/2009 | Orban, III et al. |
| 2009/0326552 A1 | 12/2009 | Diolaiti |
| 2009/0326553 A1 | 12/2009 | Mastufa et al. |
| 2009/0326556 A1 | 12/2009 | Diolaiti et al. |
| 2010/0011901 A1 | 1/2010 | Burbank |
| 2010/0036245 A1 | 2/2010 | Yu et al. |
| 2010/0063630 A1 | 3/2010 | Sutherland et al. |
| 2010/0092424 A1 | 4/2010 | Sanghvi et al. |
| 2010/0116080 A1 | 5/2010 | Pistor et al. |
| 2010/0116081 A1 | 5/2010 | Pistor et al. |
| 2010/0121148 A1 | 5/2010 | Donhowe et al. |
| 2010/0121151 A1 | 5/2010 | Donhowe et al. |
| 2010/0140500 A1 | 6/2010 | Jesseph et al. |
| 2010/0145521 A1 | 6/2010 | Prisco et al. |
| 2010/0160724 A1 | 6/2010 | Prisco |
| 2010/0161129 A1 | 6/2010 | Costa et al. |
| 2010/0191250 A1 | 7/2010 | Scott et al. |
| 2010/0191251 A1 | 7/2010 | Scott et al. |
| 2010/0198215 A1 | 8/2010 | Julian et al. |
| 2010/0198218 A1 | 8/2010 | Manzo |
| 2010/0198231 A1 | 8/2010 | Scott |
| 2010/0198232 A1 | 8/2010 | Diolaiti |
| 2010/0217284 A1 | 8/2010 | Grace |
| 2010/0228250 A1 | 9/2010 | Brogna |
| 2010/0228265 A1 | 9/2010 | Prisco |
| 2010/0228266 A1 | 9/2010 | Hourtash |
| 2010/0228284 A1 | 9/2010 | Cooper et al. |
| 2010/0241138 A1 | 9/2010 | Burbank et al. |
| 2010/0245541 A1 | 9/2010 | Zhao et al. |
| 2010/0249506 A1 | 9/2010 | Prisco |
| 2010/0249507 A1 | 9/2010 | Prisco et al. |
| 2010/0250000 A1 | 9/2010 | Blumenkranz et al. |
| 2010/0261961 A1 | 10/2010 | Scott et al. |

OTHER PUBLICATIONS

Landman, et al., Laparoscopic Partial Nephrectomy, retrieved from the Internet: URL: http://www.kidneycancerinstitute.com/PDFs/Aesculap-Nader-partial-nephrectomy%20manuscript.pdf, Oct. 9, 2010.

Da Vinci Surgical System EndoWrist Instrument & Accessory Catalog, Sep. 2010, Intuitive Surgical; product literature, 30 pages.

PCT International Search Report and Written Opinion for PCT/US2011/063082 dated Mar. 21, 2012.

U.S. 12/958,953, filed Dec. 2, 2010, US-2012-0143172-A1.

* cited by examiner

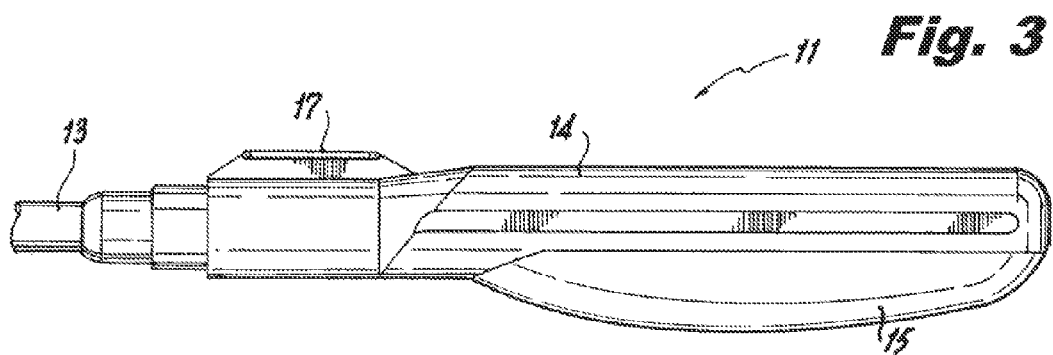
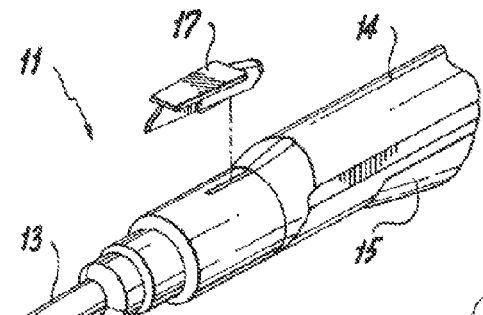
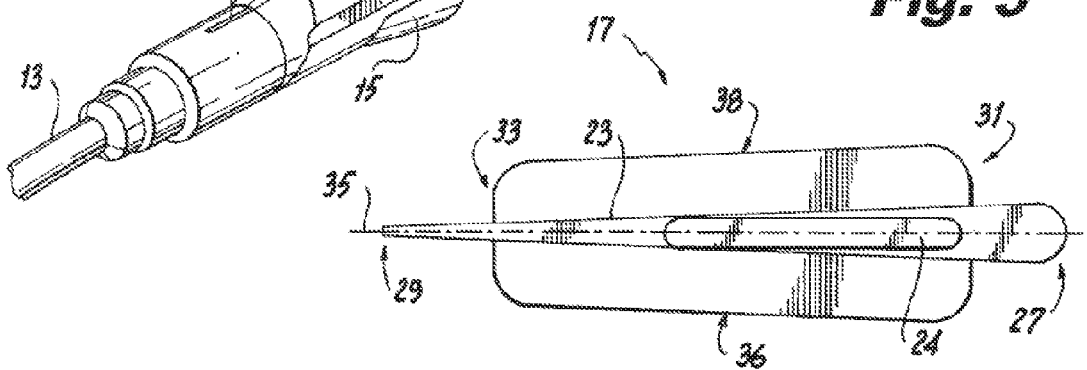
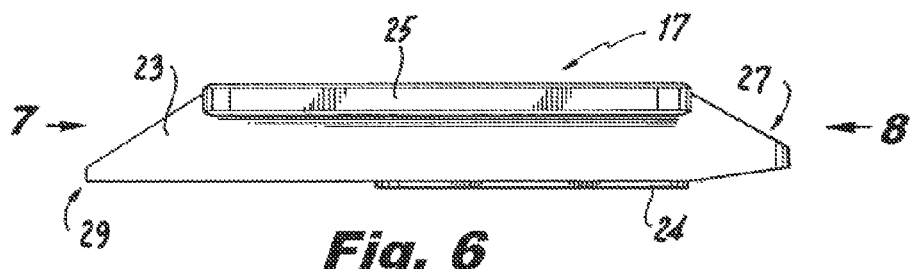
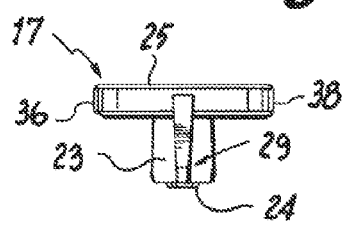
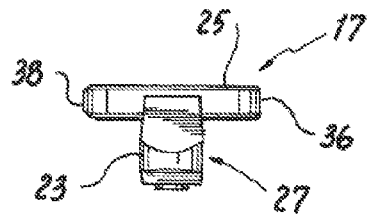

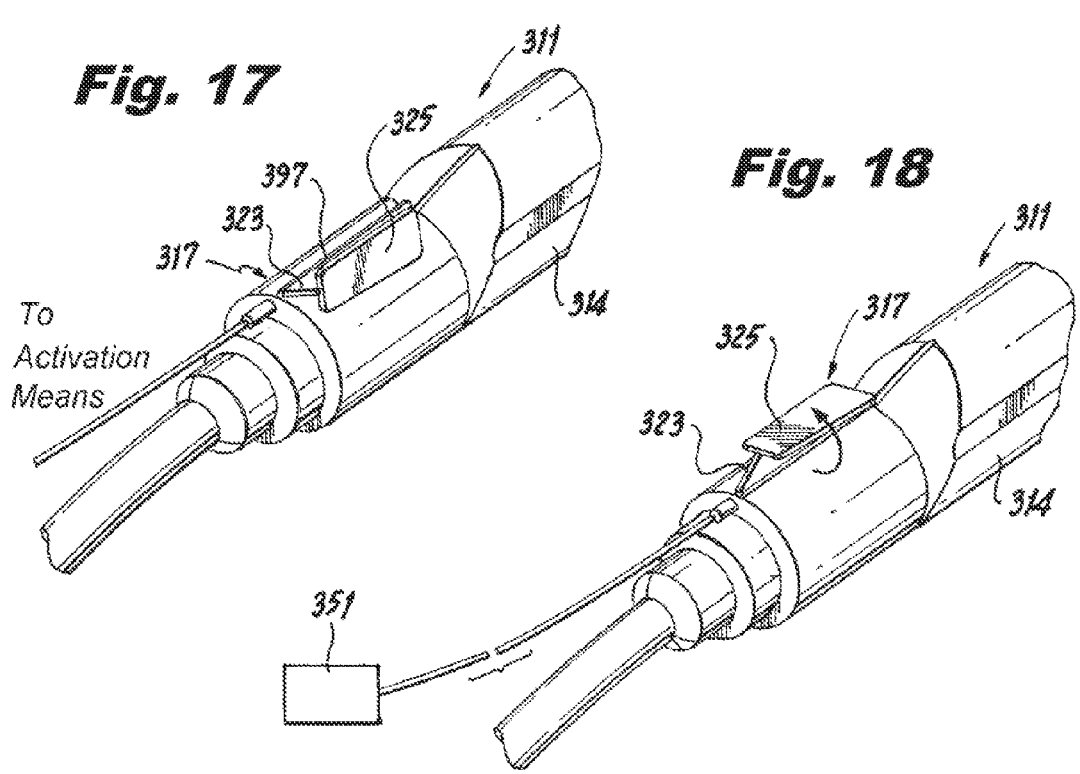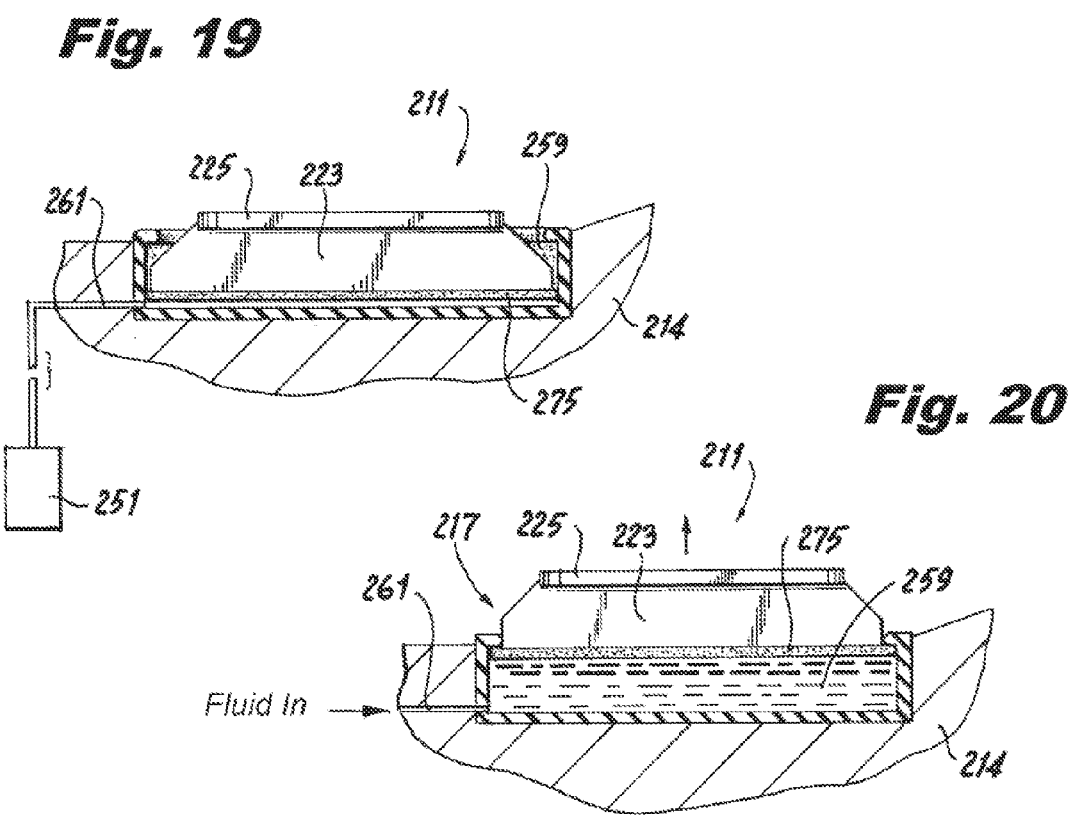

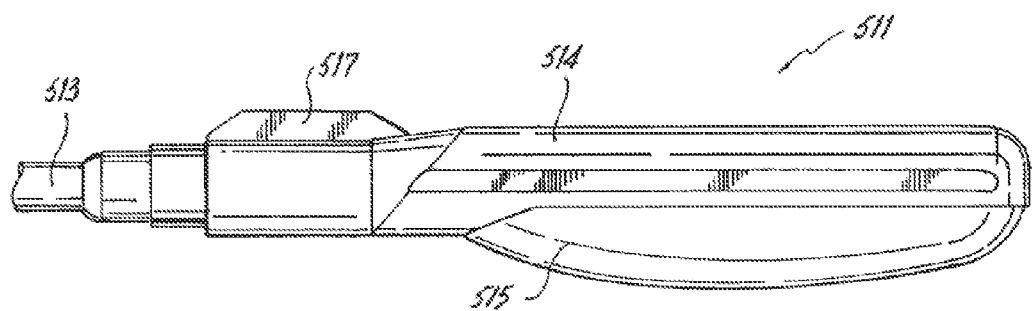
Fig. 21
Fig. 22
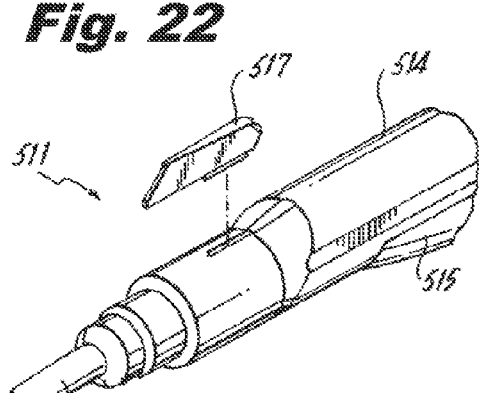
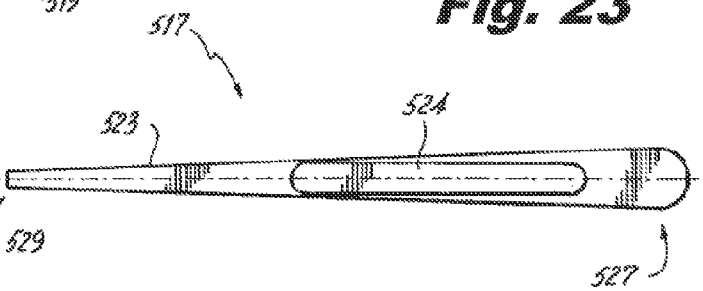
Fig. 23
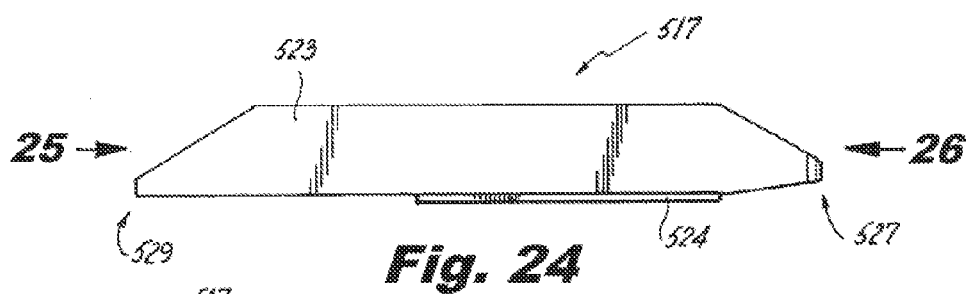
Fig. 24
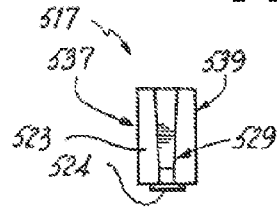
Fig. 25
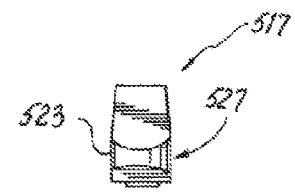
Fig. 26

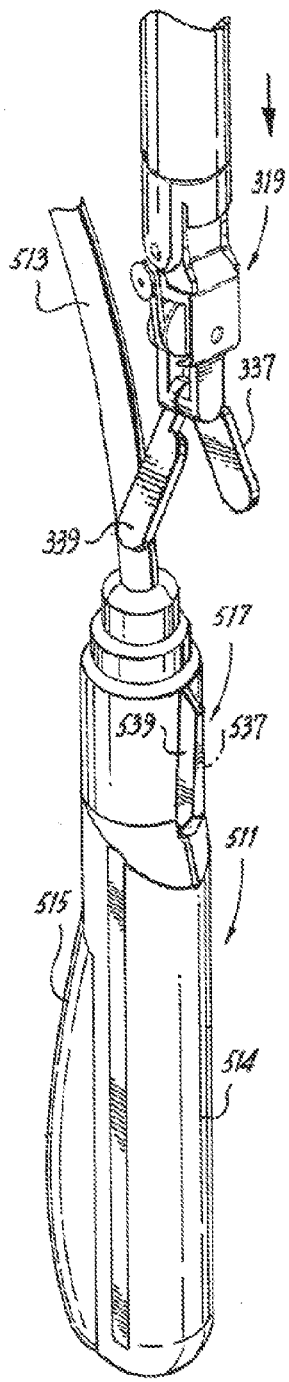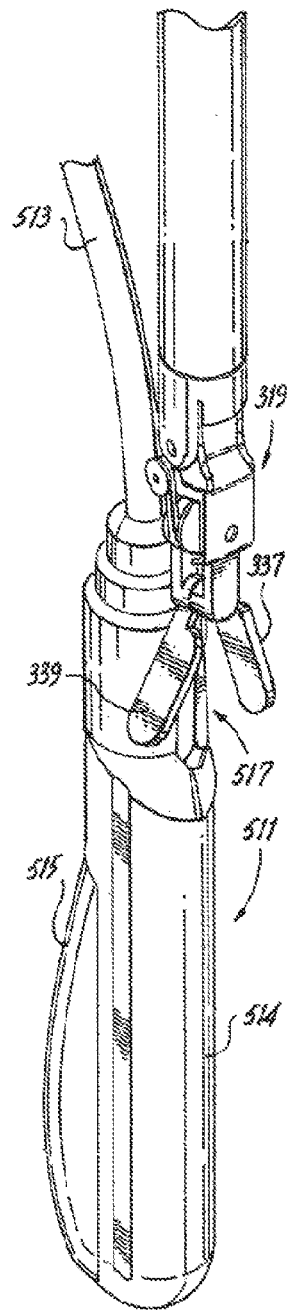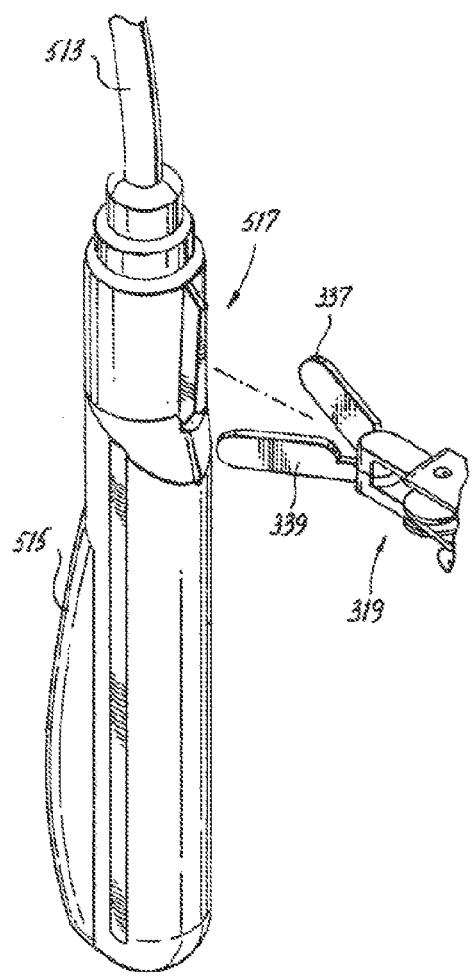
*Fig. 27*   *Fig. 28*   *Fig. 29*

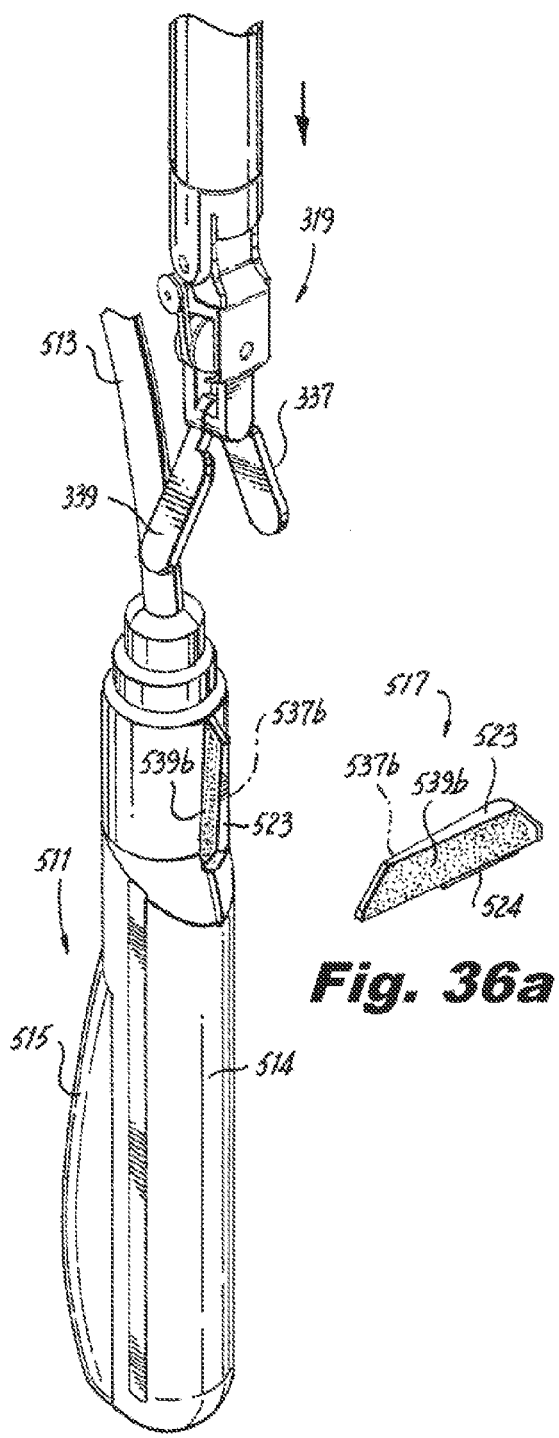
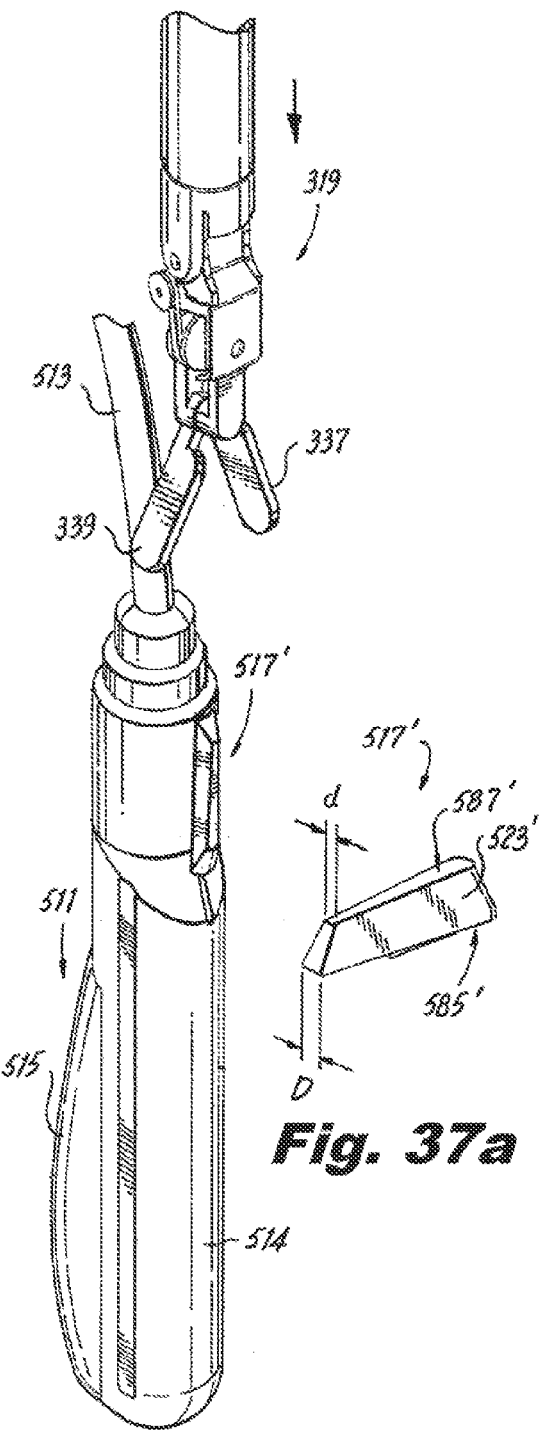

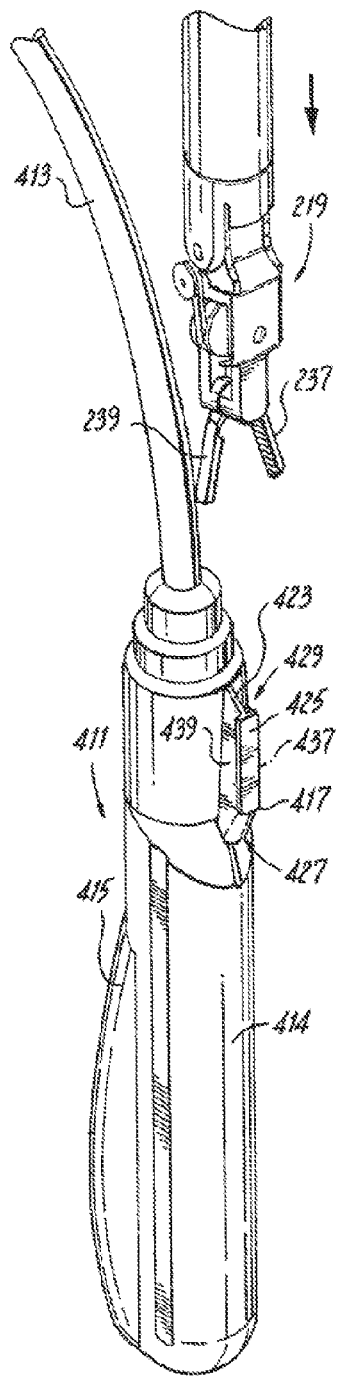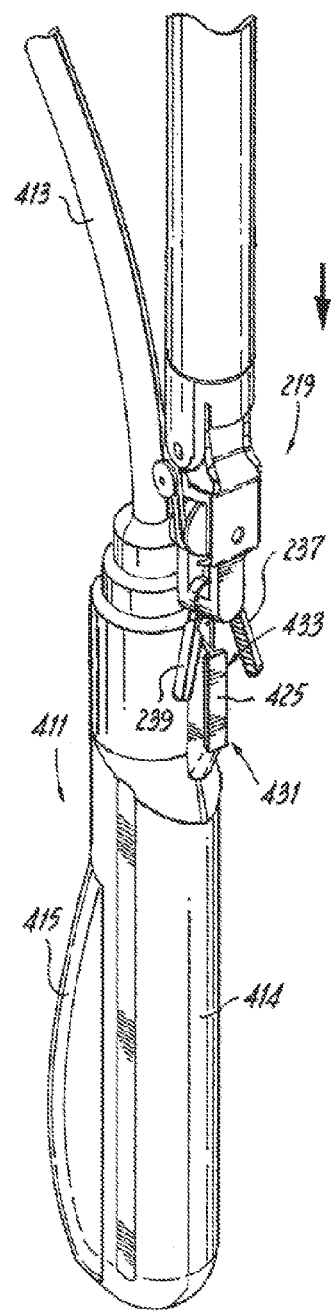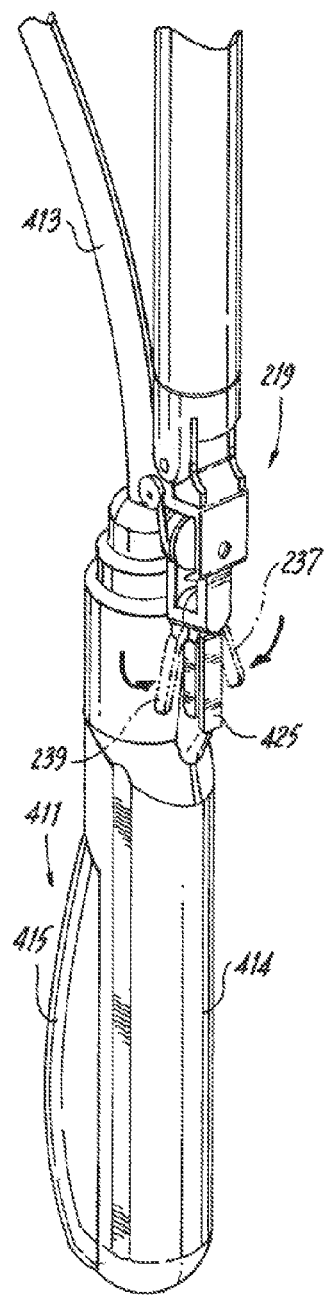
*Fig. 40*     *Fig. 41*     *Fig. 42*

ASSEMBLY FOR USE WITH SURGERY SYSTEM

CROSS REFERENCE TO RELATED APPLICATIONS

This application claims priority to and is a continuation-in-part of: (i) co-pending U.S. patent app. Ser. No. 12/958,953, filed Dec. 2, 2010; and (ii) co-pending PCT International Patent Application No. PCT/US2011/063082, filed Dec. 2, 2011, both of which are hereby incorporated by reference in their entireties.

BACKGROUND

1. Technical Field

The present disclosure relates to advantageous systems, assemblies and methods for surgery (e.g., robotic surgery) and, more particularly, to a system and method for releasably securing or attaching an assembly (e.g., a surgical or imaging assembly having a receiver member) with respect to a surgical device (e.g., with respect to a grasper member of a surgery system).

2. Background Art

Minimally invasive surgical systems or the like are known. Minimally invasive surgery typically presents some advantages compared to traditional and/or open surgery procedures (e.g., reduced scarring and/or recovery time, decreased injury/pain to the patient, decreased hospitalization time, etc.). Minimally invasive surgery is generally known under various names (e.g, endoscopy, laparoscopy, arthroscopy, etc.), with the names typically being specific to the anatomical area of the surgery. For example, laparoscopic surgery, which is one type of minimally invasive surgery, is a more recent surgical technique where operations in the abdomen are performed through small incisions (e.g., about 1.0 cm) as compared to larger incisions typically required in traditional surgical procedures.

In general, telesurgery systems allow a surgeon to operate on a patient from a remote location. Telesurgery is a general term for surgical systems (e.g., robotic surgical systems) where the surgeon uses some form of servo-mechanism to manipulate the surgical instruments movements rather than directly holding and moving some of the tools. Robotic surgical systems such as minimally invasive robotic surgical systems or the like are generally known. Telesurgery systems have been utilized for both open and endoscopic procedures.

During a minimally invasive surgical procedure (robotic or manual), tubes or the like (e.g., cannulas or trocars or other tool guides) may be inserted through the same or different incisions so that assemblies, devices, probes and/or surgical instruments/tools may be introduced to the desired surgical site. In general, many different surgical procedures can then be performed without requiring a large and/or open cavity incision as typically required by traditional surgical procedures. The laparoscopic surgical instruments generally are similar to those used in conventional (open) surgery, except that the working end of each tool is separated from its handle by an approximately 12-inch long extension tube. The surgeon (and/or robotic system) typically passes instruments through a cannula or the like and manipulates them inside the abdomen by sliding them in and out through the cannula, rotating them in the cannula, levering or pivoting the instruments in the abdominal wall and actuating end effectors on the distal end of the instruments.

In general, imaging devices or the like (e.g., ultrasound probes/transducers and/or assemblies, endoscopes, cameras, etc.) and other surgical instruments/assemblies (e.g., clamp members/instruments, grasper members/instruments, blades, needles, scissors, holder members/instruments, staplers, etc.) for use with minimally invasive surgical systems (e.g., robotic or manual) are known. For example, imaging devices such as ultrasound assemblies and/or probes or the like that are introduced to the desired surgical site provide images of the site to the surgeon. As noted, minimally invasive tools or devices are typically configured and dimensioned to be inserted through a cannula or trocar or other tool guide located in a minimally invasive incision of the patient in order to extend the surgical tools or devices to the surgical site. Exemplary minimally invasive robotic surgical systems are disclosed, for example, in U.S. Pat. Nos. 5,797,900; 5,876,325; 6,371,952 and 7,107,090; and U.S. Patent Publication Nos. 2007/0021738; 2008/0064921; 2009/0088773; 2009/0192519; 2009/0245600; 2009/0248041 and 2009/0326318; the foregoing being incorporated herein by reference in their entireties.

In general and as disclosed in the above listed references, robotic surgical systems typically include user-operable master input devices (e.g., joysticks, gloves, trigger-guns, hand-operated controllers, etc.) that allow a user to manipulate them to have a processor then cause their respectively associated slave arms or the like manipulate their respectively coupled and/or held surgical instruments and/or devices. In short, a surgeon typically performs a minimally invasive surgical procedure with a robotic system by manipulating the master input devices to control (via a processor) the robotic slave arms, which have tools, instruments, probes, etc. attached thereto. Robotic surgical systems typically also include a master display or display screen.

Current practice provides that surgeons or technicians are frequently confronted with the need to move, position, re-position, align and/or adjust various assemblies/devices/tools or the like (e.g., surgical assemblies, imaging assemblies, ultrasound probes/transducers, endoscopes, blades, etc.) during surgery (robotic or manual surgery) under difficult conditions (e.g., in confined/tight spaces, in conjunction with robotic surgical systems, etc.). Such movements/procedures can be very difficult and/or time consuming, especially when the surgical and/or imaging assemblies or the like are associated with and/or utilized along with minimally invasive surgical systems (e.g., minimally invasive robotic surgical systems).

With the foregoing in mind, those skilled in the art will understand that a need exists to provide a patient/user with an assembly for use in a surgical procedure that is capable of releasably securing or attaching to a user-operable surgical device (e.g., a user-operable surgical device associated with a minimally invasive surgery system, such as a robotic surgery system). Thus, despite efforts to date, a need remains for improved and efficient systems/methods for releasably securing or attaching an assembly for use in a surgical procedure (e.g., an imaging assembly having a receiver member) with respect to a surgical device (e.g., with respect to and for use with a grasper member of a robotic surgery system).

These and other challenges and opportunities for improvement are addressed and/or overcome by the systems, assemblies and methods of the present disclosure.

SUMMARY

The present disclosure provides advantageous systems, assemblies and methods for surgery (e.g., robotic surgery).

More particularly, the present disclosure provides improved systems and methods for releasably securing or attaching an assembly for use in a surgical procedure with respect to a user-operable surgical device. In general, the present disclosure provides improved systems and methods for releasably attaching or securing an assembly (e.g., a surgical or imaging assembly) with respect to and for use with a user-operable robotic surgery system. In exemplary embodiments, the present disclosure provides advantageous systems and methods for releasably securing or attaching an assembly having a receiver member with respect to a user-operable grasper member of a robotic or manual surgery system. In certain embodiments, the receiver member is releasably and/or detachably securable to the assembly for use in a surgical procedure (e.g., to the surgical/imaging assembly).

The present disclosure provides for an assembly for use in a surgical procedure including a housing defining at least a first groove and at least a second groove; a receiver member including an attachment section, a post member and a securing member, the post member extending from the attachment section and the securing member extending past both sides of the post member to define a substantially fin-shaped portion of the receiver member; wherein at least a first portion of the attachment section is configured and dimensioned to be releasably positioned within at least a portion of the first groove of the housing, and at least a second portion of the attachment section is configured and dimensioned to be releasably positioned within at least a portion of the second groove of the housing to releasably secure the receiver member to the housing; and wherein the substantially fin-shaped portion of the receiver member is configured and dimensioned to be releasably secured to a user-operable surgical device.

The present disclosure also provides for an assembly further including an imaging member mounted with respect to the housing; and wherein the imaging member is an ultrasound transducer. The present disclosure also provides for an assembly wherein the user-operable surgical device includes first and second end effectors, the first end effector having a first slit and the second end effector having a second slit; wherein the securing member has a first side and a second side; and wherein at least a portion of the first side of the securing member extends through the first slit and at least a portion of the second side of the securing member extends through the second slit when the user-operable surgical device is releasably secured to the receiver member.

The present disclosure also provides for an assembly wherein the securing member has a first end and a second end and the post member defines a longitudinal axis; and wherein the securing member tapers from the first end to the second end with the first end of the securing member extending a greater distance from the longitudinal axis relative to the distance that the second end of the securing member extends from the longitudinal axis.

The present disclosure also provides for an assembly wherein the post member has a first end and a second end, the post member tapering from the first end to the second end with the first end being wider than the second end.

The present disclosure also provides for an assembly wherein the housing is mounted with respect to a flexible cable; and wherein the imaging member is configured and dimensioned to capture an image of a surgical site.

The present disclosure also provides for an assembly wherein the user-operable surgical device is a minimally invasive user-operable surgical device; and wherein the housing and receiver member are configured and dimensioned to be: (i) inserted through a guide tool located in a minimally invasive incision of a patient, and (ii) moved to a surgical site within the patient by the minimally invasive user-operable surgical device.

The present disclosure also provides for an assembly wherein the user-operable surgical device includes first and second end effectors; wherein the post member has a first side and a second side; and wherein when the user-operable surgical device is releasably secured to the receiver member, at least a portion of the first side of the post member is adjacent to at least a portion of the first end effector, at least a portion of the second side of the post member is adjacent to at least a portion of the second end effector, and at least a portion of the first and second end effectors are positioned underneath the securing member.

The present disclosure also provides for an assembly wherein the post member has a first side and a second side, the first and second sides each having a grooved or textured surface. The present disclosure also provides for an assembly wherein the post member has a first side and a second side, the first and second sides each having a protrusion or extending member; wherein the user-operable surgical device includes first and second end effectors, the first and second end effectors each having a recess or concave portion; and wherein when the user-operable surgical device is releasably secured to the receiver member, at least a portion of the protrusion or extending member of the first side of the post member is positioned within at least a portion of the recess or concave portion of the first end effector, and at least a portion of the protrusion or extending member of the second side of the post member is positioned within at least a portion of the recess or concave portion of the second end effector.

The present disclosure also provides for an assembly wherein the attachment section of the receiver member is substantially U-shaped or C-shaped; wherein the attachment section extends from a first end to a second end; and wherein at least a portion of the first end of the attachment section is configured and dimensioned to be releasably positioned within at least a portion of the first groove of the housing, and at least a portion of the second end of the attachment section is configured and dimensioned to be releasably positioned within at least a portion of the second groove of the housing to releasably secure the receiver member to the housing.

The present disclosure also provides for an assembly wherein the first end of the attachment section includes an inner portion that extends inwardly toward the center of the attachment section, and the second end of the attachment section includes an inner portion that extends inwardly toward the center of the attachment section.

The present disclosure also provides for an assembly wherein the first and second ends of the attachment section flex outwardly when the attachment section is positioned around the housing to releasably secure the receiver member to the housing. The present disclosure also provides for an assembly wherein the attachment section includes a hinge that facilitates the first and second ends of the attachment member to flex outwardly when the attachment section is positioned around the housing.

The present disclosure also provides for an assembly wherein the attachment section includes a top side having a substantially planar region; and wherein the post member extends from the substantially planar region of the top side of the attachment section.

The present disclosure also provides for an assembly wherein the housing further comprises at least a third groove and at least a fourth groove; and wherein at least a first portion of the attachment section is configured and dimensioned to be releasably positioned within at least a portion of the third groove of the housing, and at least a second portion of the attachment section is configured and dimensioned to be releasably positioned within at least a portion of the fourth groove of the housing to releasably secure the receiver member to the housing.

The present disclosure also provides for an assembly for use in a surgical procedure including a housing defining at least a first groove and at least a second groove; a receiver member including an attachment section and a post member, the post member extending from the attachment section; wherein the post member has a first end and a second end, the post member tapering from the first end to the second end with the first end being wider than the second end; wherein at least a first portion of the attachment section is configured and dimensioned to be releasably positioned within at least a portion of the first groove of the housing, and at least a second portion of the attachment section is configured and dimensioned to be releasably positioned within at least a portion of the second groove of the housing to releasably secure the receiver member to the housing; and wherein the tapered post member of the receiver member is configured and dimensioned to be releasably secured to a user-operable surgical device.

The present disclosure also provides for an assembly further including an imaging member mounted with respect to the housing; and wherein the imaging member is an ultrasound transducer. The present disclosure also provides for an assembly wherein the user-operable surgical device includes first and second end effectors; wherein the post member has a first side and a second side; and wherein when the user-operable surgical device is releasably secured to the receiver member, at least a portion of the first side of the post member is adjacent to at least a portion of the first end effector, and at least a portion of the second side of the post member is adjacent to at least a portion of the second end effector.

The present disclosure also provides for an assembly wherein the post member has a top side and a bottom side, the post member tapering from the bottom side to the top side with the bottom side being wider than the top side.

The present disclosure also provides for an assembly wherein the housing is mounted with respect to a flexible cable; wherein the user-operable surgical device is a minimally invasive user-operable surgical device; wherein the housing and receiver member are configured and dimensioned to be: (i) inserted through a guide tool located in a minimally invasive incision of a patient, and (ii) moved to a surgical site within the patient by the minimally invasive user-operable surgical device; and wherein the imaging member is configured and dimensioned to capture an image of the surgical site.

The present disclosure also provides for an assembly wherein the post member has a first side and a second side, the first and second sides each having a grooved or textured surface. The present disclosure also provides for an assembly wherein the post member has a first side and a second side, the first and second sides each having a protrusion or extending member; wherein the user-operable surgical device includes first and second end effectors, the first and second end effectors each having a recess or concave portion; and wherein when the user-operable surgical device is releasably secured to the receiver member, at least a portion of the protrusion or extending member of the first side of the post member is positioned within at least a portion of the recess or concave portion of the first end effector, and at least a portion of the protrusion or extending member of the second side of the post member is positioned within at least a portion of the recess or concave portion of the second end effector.

The present disclosure also provides for an assembly wherein the attachment section of the receiver member is substantially U-shaped or C-shaped; wherein the attachment section extends from a first end to a second end; and wherein at least a portion of the first end of the attachment section is configured and dimensioned to be releasably positioned within at least a portion of the first groove of the housing, and at least a portion of the second end of the attachment section is configured and dimensioned to be releasably positioned within at least a portion of the second groove of the housing to releasably secure the receiver member to the housing.

The present disclosure also provides for an assembly wherein the first end of the attachment section includes an inner portion that extends inwardly toward the center of the attachment section, and the second end of the attachment section includes an inner portion that extends inwardly toward the center of the attachment section.

The present disclosure also provides for an assembly wherein the first and second ends of the attachment section flex outwardly when the attachment section is positioned around the housing to releasably secure the receiver member to the housing.

The present disclosure also provides for an assembly wherein the attachment section includes a hinge that facilitates the first and second ends of the attachment member to flex outwardly when the attachment section is positioned around the housing. The present disclosure also provides for an assembly wherein the attachment section includes a top side having a substantially planar region; and wherein the post member extends from the substantially planar region of the top side of the attachment section.

The present disclosure also provides for an assembly wherein the housing further includes at least a third groove and at least a fourth groove; and wherein at least a first portion of the attachment section is configured and dimensioned to be releasably positioned within at least a portion of the third groove of the housing, and at least a second portion of the attachment section is configured and dimensioned to be releasably positioned within at least a portion of the fourth groove of the housing to releasably secure the receiver member to the housing.

The present disclosure also provides for an imaging assembly including a housing defining at least a first groove and at least a second groove; an imaging member mounted with respect to the housing; a receiver member including an attachment section, a post member and a securing member, the post member extending from the attachment section and the securing member extending past both sides of the post member to define a substantially fin-shaped portion of the receiver member; wherein the securing member has a first end and a second end and the post member defines a longitudinal axis; wherein the securing member tapers from the first end to the second end with the first end of the securing member extending a greater distance from the longitudinal axis relative to the distance that the second end of the securing member extends from the longitudinal axis; wherein the attachment section of the receiver member is substantially U-shaped or C-shaped; wherein the attachment section extends from a first end to a second end; wherein the first end of the attachment section includes an inner portion that extends inwardly toward the center of the attachment section, and the second end of the attachment section includes an inner portion that extends inwardly toward the center of the attachment section; wherein at least a portion of the inner portion of the first end of the attachment section is configured and dimensioned to be releasably positioned within at least a portion of the first groove of the housing, and at least a portion of the inner portion of the second end of the attachment section is configured and dimensioned to be releasably positioned within at least a portion of the second groove of the housing to releasably secure the receiver member to the housing; and wherein the substantially fin-shaped receiver member is configured and dimensioned to be releasably secured to a user-operable surgical device.

Additional advantageous features, functions and applications of the disclosed systems, assemblies and methods of the present disclosure will be apparent from the description which follows, particularly when read in conjunction with the appended figures.

BRIEF DESCRIPTION OF THE DRAWINGS

Exemplary embodiments of the present disclosure are further described with reference to the appended figures. It is to be noted that the various features and combinations of features described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein:

FIG. 3 is a side view of the assembly of FIG. 1;

FIG. 4 is a partial side perspective view of the assembly of FIG. 1, with the receiver member unattached;

FIG. 5 is a bottom view of the receiver member of the assembly of FIG. 1;

FIG. 6 is a side view of the receiver member of FIG. 5;

FIG. 7 is a proximal end view of the receiver member of FIG. 5;

FIG. 8 is a distal end view of the receiver member of FIG. 5;

FIG. 17 is a partial side perspective view of an alternative embodiment of an assembly for use in a surgical procedure according to the present disclosure, the receiver member of the assembly in the folded position;

FIG. 18 is a partial side perspective view of the assembly of FIG. 17, the receiver member of the assembly in the un-folded position;

FIG. 19 is a partial sectional side view of an alternative embodiment of an assembly for use in a surgical procedure according to the present disclosure, the receiver member of the assembly in the retracted position; and FIG. 20 is a partial sectional side view of the assembly of FIG. 19, the receiver member of the assembly in the un-retracted position;

FIG. 21 is a side view of another exemplary assembly for use in a surgical procedure in accordance with the present disclosure;

FIG. 22 is a partial side perspective view of the assembly of FIG. 21, with the receiver member unattached;

FIG. 23 is a bottom view of the receiver member of the assembly of FIG. 21;

FIG. 24 is a side view of the receiver member of FIG. 23;

FIG. 25 is a proximal end view of the receiver member of FIG. 23;

FIG. 26 is a distal end view of the receiver member of FIG. 23;

FIGS. 27-29 are side perspective views of the assembly of FIG. 21 with a user-operable surgical device, prior to attachment thereto;

FIG. 36 is a side perspective views of another exemplary assembly for use in a surgical procedure, along with a user-operable surgical device, prior to attachment thereto;

FIG. 36A is a side perspective view of the receiver member of the assembly of FIG. 36;

FIG. 37 is a side perspective views of another exemplary assembly for use in a surgical procedure, along with a user-operable surgical device, prior to attachment thereto;

FIG. 37A is a side perspective view of the receiver member of the assembly of FIG. 37;

FIGS. 40-42 are side perspective views of another exemplary assembly for use in a surgical procedure, along with a user-operable surgical device, prior to and during attachment thereto;

DESCRIPTION OF EXEMPLARY EMBODIMENTS

Figure 1:
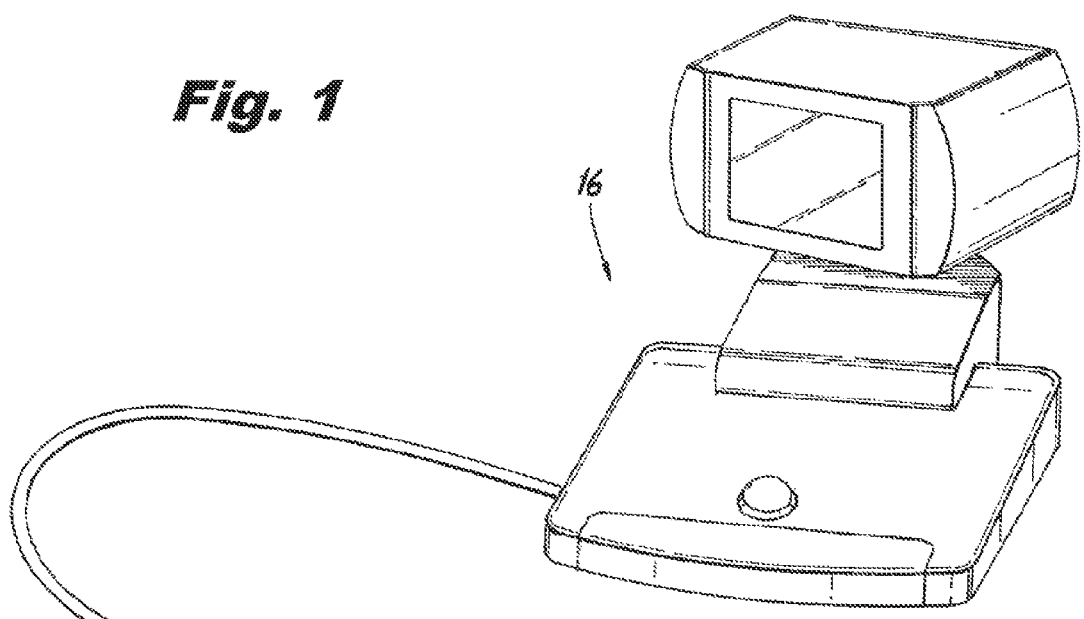
FIG. 1 is a side perspective view of an exemplary assembly for use in a surgical procedure in accordance with the present disclosure.
Figure 2:
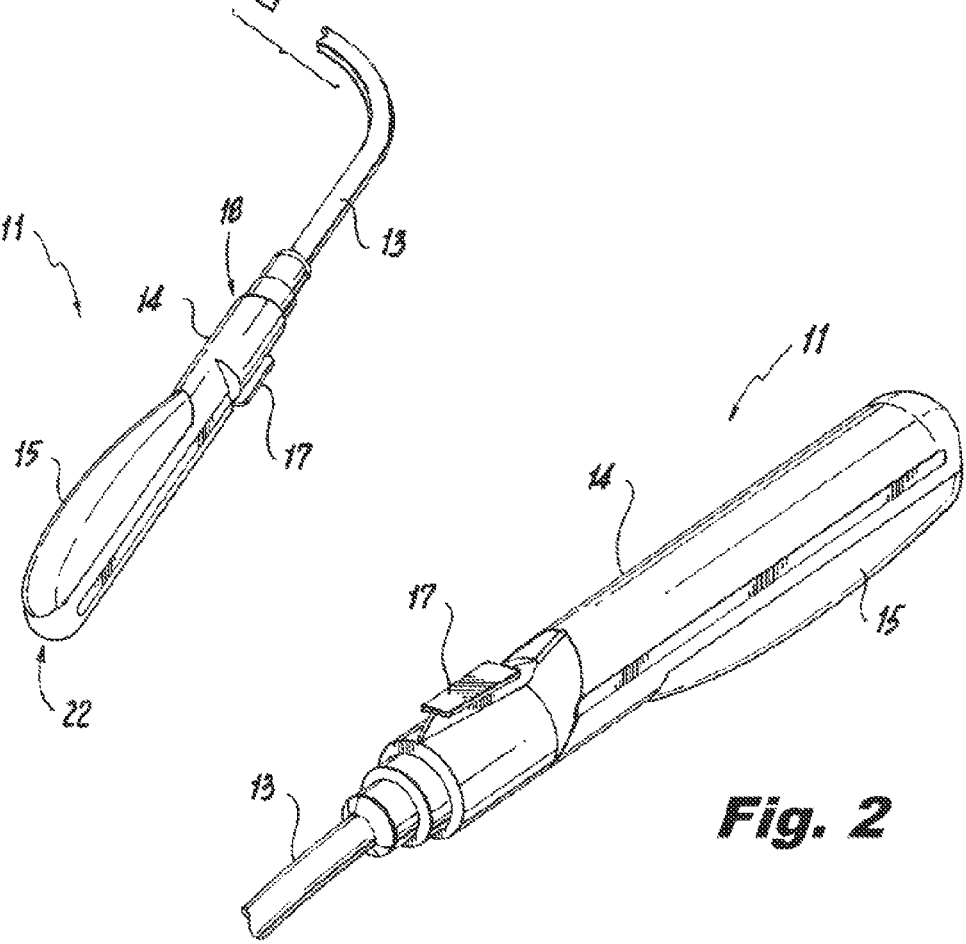
FIG. 2 is a side perspective view of the assembly of FIG. 1.

The exemplary embodiments disclosed herein are illustrative of advantageous assemblies (e.g., imaging or surgical assemblies) for use with surgery systems and methods/techniques thereof. It should be understood, however, that the disclosed embodiments are merely exemplary of the present disclosure, which may be embodied in various forms. Therefore, details disclosed herein with reference to exemplary assemblies/systems and associated methods/techniques of assembly and use are not to be interpreted as limiting, but merely as the basis for teaching one skilled in the art how to make and use the advantageous assemblies/systems and/or alternative surgical and/or imaging devices of the present disclosure.

The present disclosure provides improved systems, assemblies and methods for surgery (e.g., robotic surgery). More particularly, the present disclosure provides advantageous systems and methods for releasably attaching or securing an assembly (e.g., an imaging or surgical assembly) with respect to a user-operable surgical device. In general, the present disclosure provides systems and methods for releasably attaching or securing an assembly for use in a surgical procedure with respect to and for use with a user-operable robotic surgery system. In exemplary embodiments, the present disclosure provides advantageous systems and methods for releasably attaching or securing an assembly having a receiver member with respect to a user-operable grasper member of a robotic or manual surgery system. In certain embodiments, the receiver member is releasably and/or detachably securable to the surgical/imaging assembly.

In exemplary embodiments, the assembly for use in a surgical procedure includes at least one receiver member, the at least one receiver member configured and dimensioned to be releasably secured to a user-operable surgical device (e.g., a user-operable grasper member of a robotic or manual surgery system). In general, the assembly for use in a surgical procedure includes an imaging member (e.g., ultrasound probe/transducer, endoscope, camera, etc.) and/or a surgical instrument/tool/device (e.g., clamp members/instruments, blades, needles, scissors, holder members, staplers, etc.) or the like, and/or some other treatment instrument/device.

In exemplary embodiments, the assembly for use in a surgical procedure includes at least one receiver member, component or protrusion (e.g., a T-shaped or fin-shaped protrusion) that allows the assembly to be releasably secured with respect to a user-operable surgical device. A user may then manipulate the user-operable surgical device to move/position the releasably secured surgical and/or imaging assembly to any desired position and/or location. For example, the assembly may include a T-shaped or fin-shaped protrusion at one end that extends from the assembly to allow the user operable surgical device to releasably secure or attach to at least a portion of the protrusion of the assembly. The receiver member may define at least one cavity, recess, channel or receiving feature/surface that allows the user-operable surgical device to releasably secure to the surgical or imaging assembly. As noted above and in certain embodiments, the receiver member is releasably and/or detachably securable to the surgical/imaging assembly.

Current practice provides that it is often very difficult and/or time consuming for a surgeon or technician to move, position, re-position, align and/or adjust assemblies or the like (e.g., surgical or imaging assemblies) during surgery, especially when the assemblies or the like are associated with and/or utilized along with minimally invasive surgical systems (e.g., minimally invasive robotic surgical systems). In exemplary embodiments, the present disclosure provides for improved and effective systems/designs for assemblies that are easily releasably attached or secured to a user-operable surgical device (e.g., a user-operable surgical device associated with a minimally invasive surgery system, such as a robotic surgery system), thereby providing a significant manufacturing, commercial and/or surgical advantage as a result. Furthermore, the exemplary assemblies/systems may also be capable of attaching, mounting and/or mating with respect to other user-operable surgical devices, thereby providing a significant manufacturing, commercial and/or surgical advantage as a result.

Referring now to the drawings, like parts are marked throughout the specification and drawings with the same reference numerals, respectively. Drawing figures are not necessarily to scale and in certain views, parts may have been exaggerated for purposes of clarity.

Figure 9:
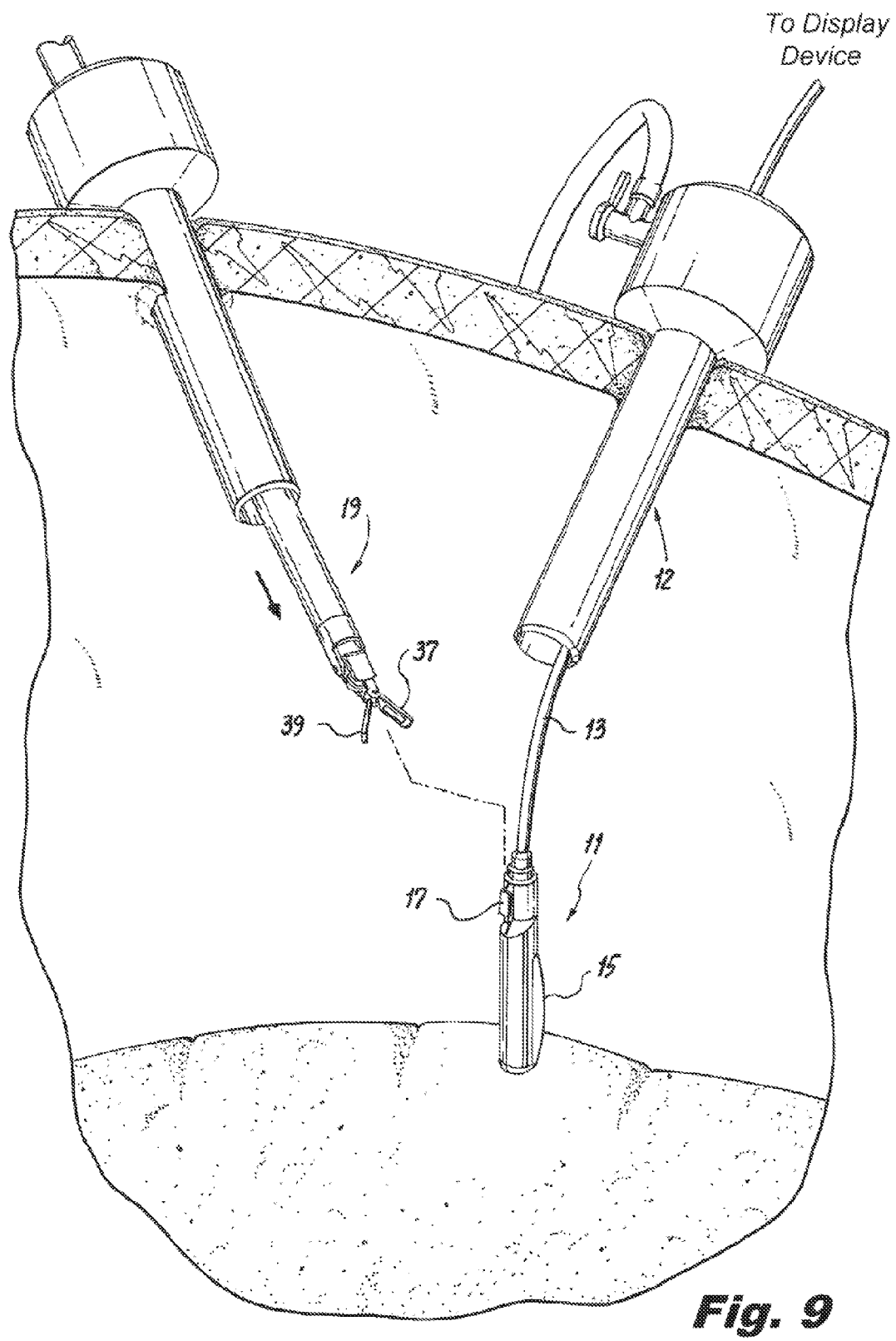
FIG. 9 is an in situ side perspective view of an exemplary user-operable surgical device for use with the exemplary assembly of FIG. 1.
Figure 10:
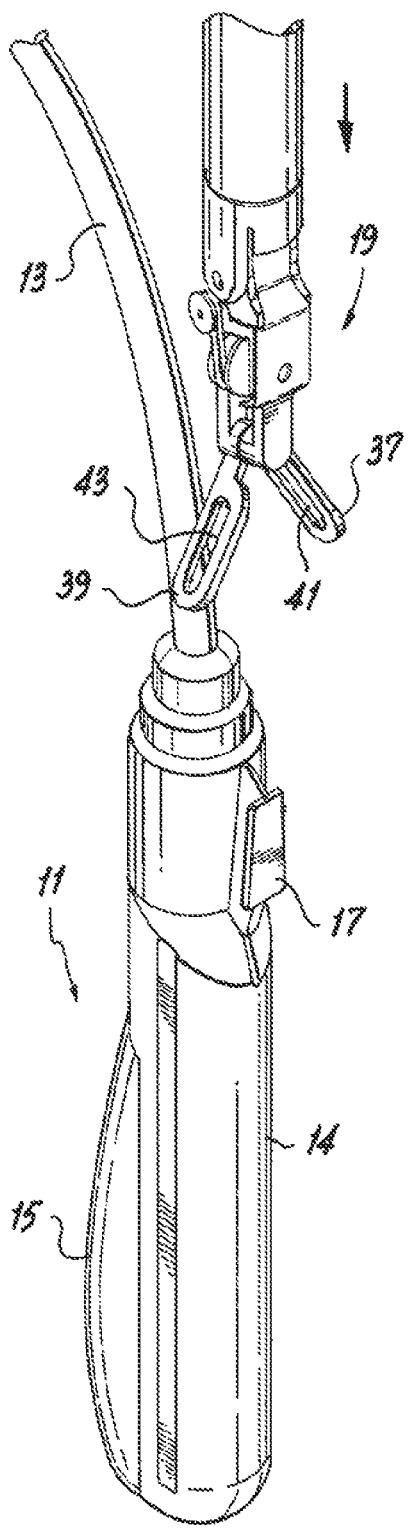
FIGS. 10-11 are side perspective views of the assembly of FIG. 1 with the user-operable surgical device of FIG. 9 prior to attachment thereto.
Figure 11:
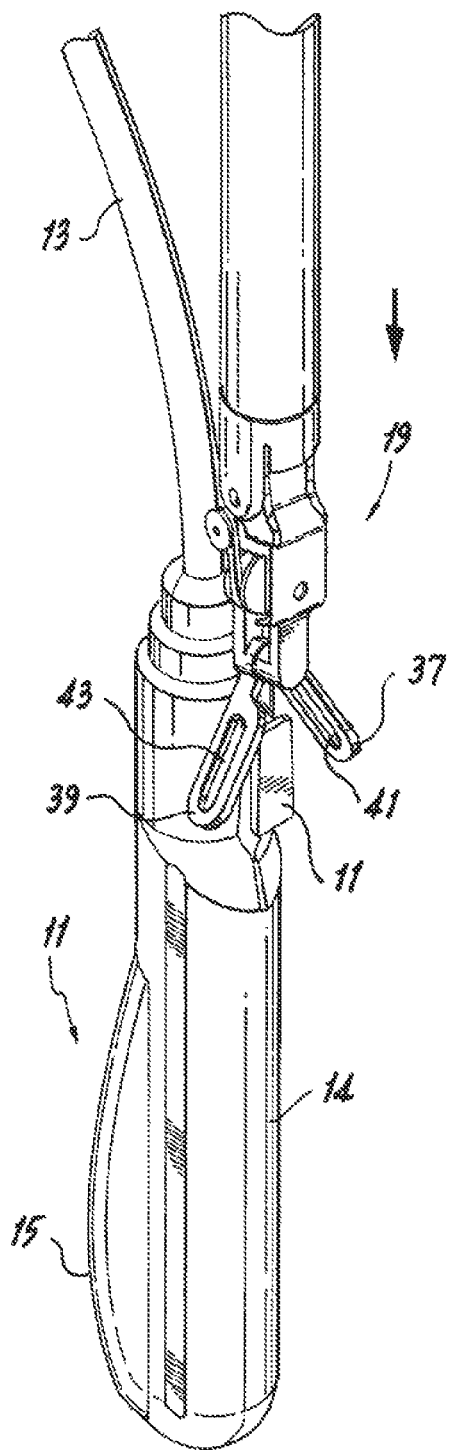
Figure 59:
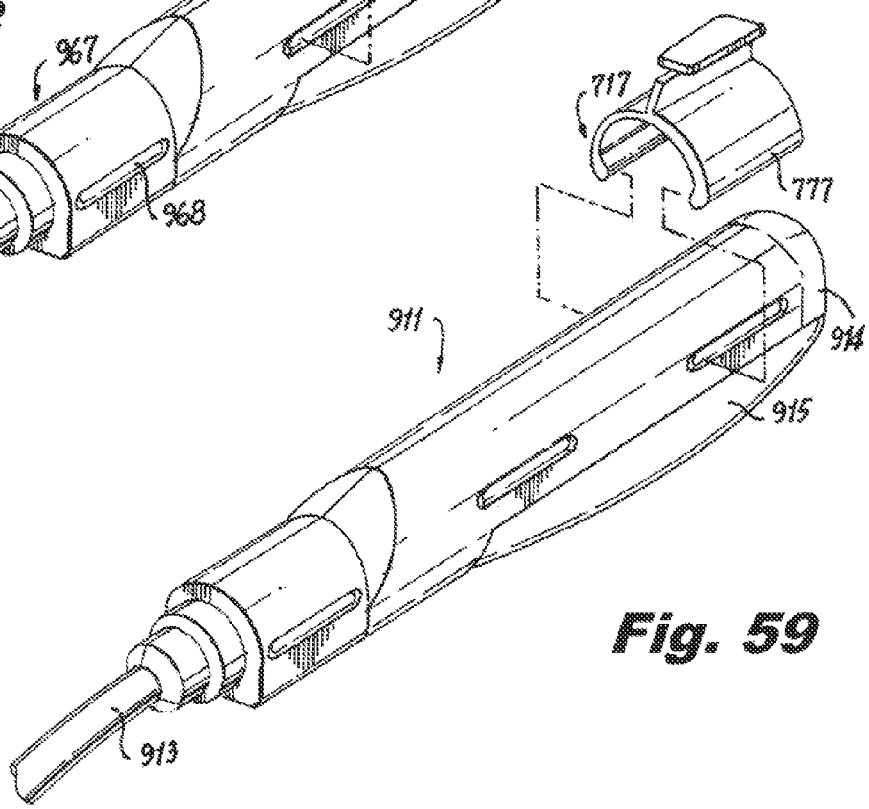

FIGS. 1-59 depict exemplary embodiments of the advantageous assemblies, systems and methods of the present disclosure. As shown in FIGS. 1-4, an exemplary assembly 11 for use in a surgical procedure is typically attached or mounted with respect to a flexible cable 13 or the like. In general, cable 13 allows assembly 11 to be introduced to a surgical site (e.g., in a minimally invasive manner) for imaging and/or surgical purposes or the like (see, e.g., FIGS. 9 and 13). For example, assembly 11 with respective cable 13 attached thereto is typically configured and dimensioned to be inserted through a cannula or trocar or other tool guide 12 (FIG. 9) located in a minimally invasive incision of a patient in order to allow a surgeon or technician to extend at least a portion of the assembly 11 to a surgical site for imaging and/or surgical purposes. Assembly 11 may also be inserted through a body orifice, or utilized in other surgical procedures (e.g., open surgery).

In exemplary embodiments, assembly 11 is connected to and/or in communication with a display device/assembly 16 for displaying images of the surgical site, the display device 16 generally in communication with a processor and being positioned outside of the body of the patient. In one embodiment, cable 13 connects imaging assembly 11 to display device 16 for displaying captured images of the surgical site. However, other variations and modifications are possible. It is noted that assembly 11 is to be construed broadly to include image capture components or members and their associated wiring, cabling, circuitry, hardware and/or display devices. Assembly 11 may relay image data via wired or wireless connections to display device 16 (e.g., to display device 16 positioned outside of the body of the patient).

Exemplary assembly 11 takes the form of an imaging assembly (e.g., an ultrasound imaging assembly), although the present disclosure is not limited thereto. Rather, assembly 11 may take a variety of forms, including, without limitation, an endoscopic imaging assembly, an optical imaging assembly, an infrared imaging assembly, a camera-based imaging assembly or the like. It is noted that assembly 11 may or may not include an imaging member or the like. For example, assembly 11 may include a surgical member/instrument/tool/device (e.g., clamp members/instruments, blades, needles, scissors, holder members, staplers, grasper members, etc.) or the like, and/or some other treatment member/instrument/device (e.g., for use in a surgical procedure).

As shown in FIGS. 1-4, exemplary assembly 11 for use in a surgical procedure includes housing 14. In one embodiment, assembly 11 takes the form of an imaging assembly 11 (e.g., an ultrasound imaging assembly), although the present disclosure is not limited thereto. Rather and as noted above, assembly 11 for use in a surgical procedure may take a variety of forms. Assembly 11 is typically configured and dimensioned to be inserted through a cannula or trocar or other tool guide 12 located in a minimally invasive incision of a patient in order to allow a surgeon or technician to extend the assembly 11 to a surgical site for imaging and/or surgical/treatment purposes.

In exemplary embodiments, housing 14 is configured and dimensioned to house, secure and/or mount with respect to an imaging member 15. Exemplary imaging member 15 takes the form of an ultrasound transducer, although the present disclosure is not limited thereto. Rather, imaging member 15 may take a variety of forms (e.g., endoscope, camera, etc.). In general, imaging member 15 is configured and dimensioned to capture/obtain images of the surgical site.

In exemplary embodiments, imaging member 15 is an ultrasound transducer that includes a plurality of ultrasonic energy generation elements. As shown in FIG. 1, ultrasound transducer 15 typically extends to the distal end 22 of the housing 14 of ultrasound imaging assembly 11. However and as noted above, the present disclosure is not to be limited to an ultrasonic imaging device/assembly. In exemplary embodiments, ultrasound transducer 15 is configured and dimensioned to obtain two-dimensional or three-dimensional images of the desired surgical site (e.g., in a minimally invasive manner). For example, assembly 11 with ultrasound transducer 15 is typically configured and dimensioned to be inserted through a cannula or trocar or other tool guide 12 located in a minimally invasive incision of a patient in order to allow a surgeon or technician to extend the ultrasound transducer 15 to a surgical site so that the assembly 11 can relay captured ultrasound image data to outside the patient body. Assembly 11 may also be used in other surgical procedures, e.g., open surgery procedures, for imaging and/or surgical purposes.

As depicted in FIGS. 1-13, exemplary assembly 11 (e.g., ultrasound imaging assembly) also includes a receiver member 17. In one embodiment, the housing 14 and the receiver member 17 are of unitary construction with respect to each other (e.g., the receiver member 17 is integrally formed from the housing 14), although the present disclosure is not limited thereto. Alternatively, receiver member 17 may be separately fabricated and then secured, attached or mounted with respect to (e.g., welded) housing 14 (FIG. 4).

In general, receiver member 17 is configured and dimensioned to be releasably secured or attached to a user-operable surgical device 19 (e.g., a user-operable grasper member of a robotic or manual surgery system), as further discussed below in conjunction with FIGS. 9-13. As such, a user may then manipulate the user-operable surgical device 19 to move/position the releasably secured imaging assembly 11 to any desired position and/or location (e.g., in a minimally invasive manner within the surgical site for imaging, surgical and/or diagnostic purposes).

In exemplary embodiments, the receiver member 17 is a substantially T-shaped or fin-shaped component or protrusion that extends from the housing 14 (e.g., from or near the proximal end 18 of housing 14) to allow the user operable surgical device 19 to releasably secure or attach to at least a portion of the receiver member 17. The receiver member 17 may also define at least one cavity, recess, channel or receiving feature/surface that allows the user-operable surgical device 19 to releasably secure to the assembly 11.

In exemplary embodiments and as shown in FIGS. 5-8, receiver member 17 includes a post member 23 that extends from housing 14, and a securing member 25 that extends beyond or past both sides of the post member 23 to define a substantially T-shaped or fin-shaped component or protrusion (i.e., receiver member 17) that extends from the housing 14 (e.g., extends from at or near the proximal end 18 of housing 14). In general, the post member 23 and the securing member 25 are of unitary construction with respect to each other, although the present disclosure is not limited thereto. Post member 23 may also include an attachment member 24, the attachment member 24 being configured and dimensioned to be attached, secured or mounted with respect to the housing 14 (e.g., with respect to a groove or slot of housing 14) of the assembly 11.

The post member 23 has a first end 27 and a second end 29, with the first end 27 typically being wider (e.g., laterally wider) than the second end 29 (FIG. 5) (e.g., the post member 23 tapers from the first end 27 to the second end 29). The securing member 25 has a first end 31 and a second end 33, with the first end 31 typically extending (e.g., laterally) a greater distance beyond the longitudinal axis 35 of the post member 23 relative to the extension of the second end 33 of the securing member 25 beyond axis 35 (FIG. 5) (e.g., the securing member 25 tapers from the first end 31 to the second end 33).

As noted above, assembly 11 may be utilized in conjunction with a user-operable surgical device 19 (FIGS. 9-13), such as, for example, a user-operable grasper member of a robotic or manual surgery system (e.g., a minimally invasive surgery system). For example, a technician or surgeon can operate/move user-operable surgical device 19 either manually (e.g., by operating a conventional laparoscopic surgical device 19) or by robotic tele-surgery operation (e.g., utilizing a robotic surgery system such as a minimally invasive robotic surgery system) within or near the surgical site to releasably secure or attach the user-operable surgical device 19 to assembly 11. Once the user-operable surgical device 19 is releasably secured or attached to the assembly 11, a user may then move/position (e.g., manually or tele-surgically) the assembly 11 to any desired position and/or location (e.g., in a minimally invasive manner within the surgical site for imaging, surgical and/or diagnostic purposes).

As noted above, exemplary robotic surgical systems (e.g., minimally invasive robotic surgical systems) and their operations/movements thereof are disclosed and described in U.S. Pat. Nos. 5,797,900; 5,876,325; 6,371,952 and 7,107,090; and U.S. Patent Publication Nos. 2007/0021738; 2008/0064921; 2009/0088773; 2009/0192519; 2009/0245600; 2009/0248041 and 2009/0326318; the entire contents of each being hereby incorporated by reference in their entireties.

Figure 12:
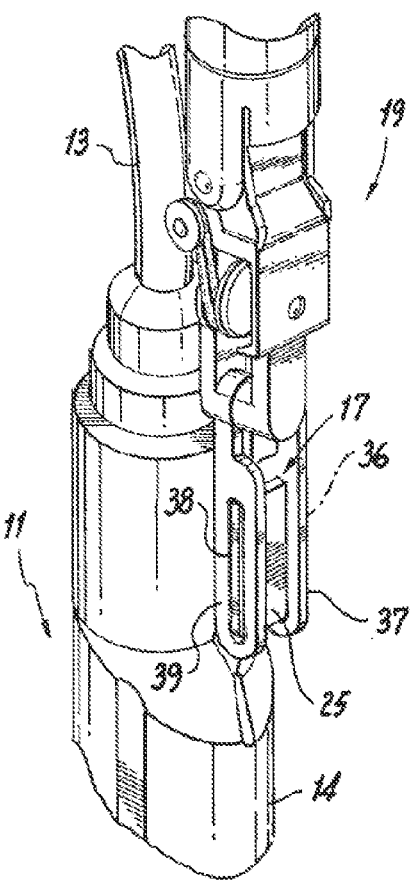
FIG. 12 is a partial side perspective view of the assembly of FIG. 1 with the user-operable surgical device of FIG. 9 attached thereto.
Figure 13:
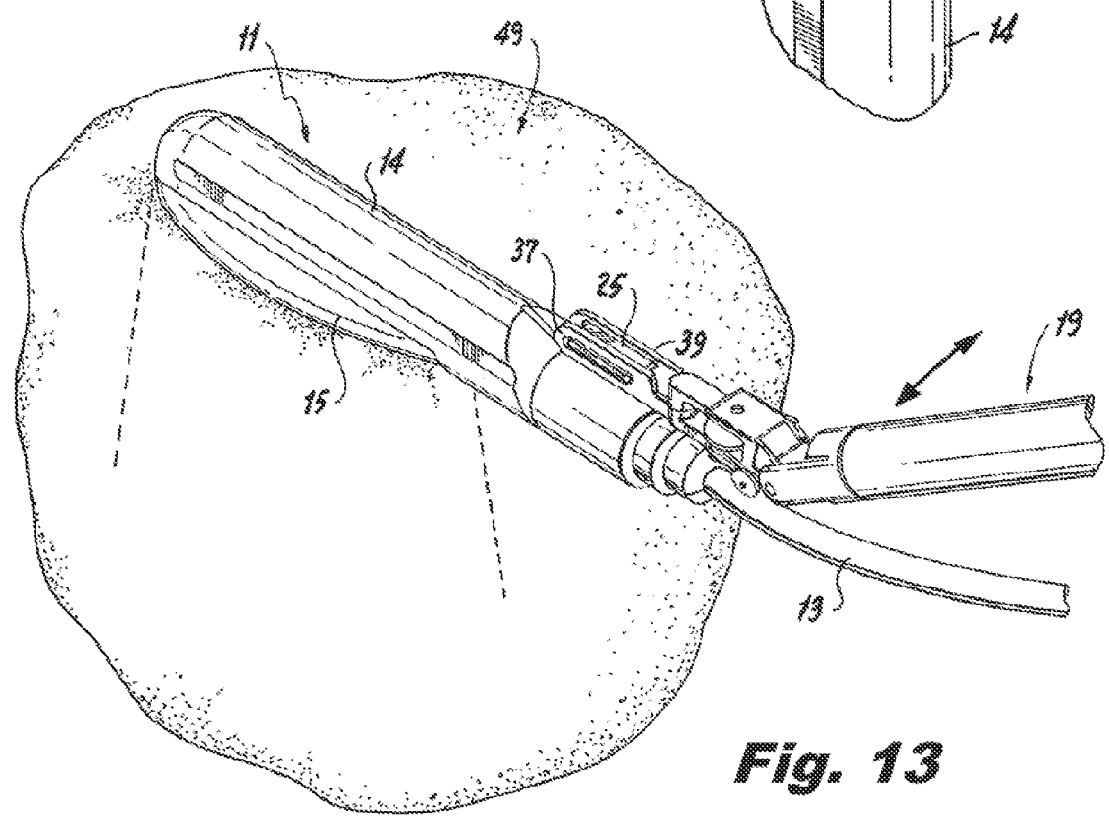
FIG. 13 is an in situ side perspective view of the assembly of FIG. 1 with the user-operable surgical device of FIG. 9 attached thereto.

In one embodiment, the user-operable grasper member 19 includes first and second end effectors 37, 39 (e.g., first and second jaws or grasping members 37, 39), with each end effector 37, 39 having respective slots 41, 43. As such, a user may operate the user-operable grasper member 19 (e.g., either manually or tele-surgically) to firstly open or widen the first and second end effectors 37, 39, and then secondly to position the slots 41, 43 of grasper member 19 adjacent to the left side and right side 36, 38 of securing member 25, respectively. The user may then operate the grasper member 19 to then close the end effectors 37, 39 so that at least a portion of the left side 36 of securing member 25 is releasably secured within slot 41, and at least a portion of the right side 38 of securing member 25 is releasably secured within slot 43 (FIGS. 12-13). In exemplary embodiments, at least a portion of left side 36 extends through slot 41 and at least a portion of right side 38 extends through slot 43 after the end effectors 37, 39 are releasably secured to receiver member 17.

In this way, user-operable surgical device 19 is now releasably secured or attached to receiver member 17 of assembly 11, and a user may then move/position the assembly 11 to any desired position and/or location (e.g., for imaging/surgical purposes) by operating device 19 (e.g., either manually or tele-surgically). For example and as shown in FIG. 13, a user may then move and/or position the assembly 11 over, across and/or adjacent to at least a portion of tissue or organ 49 of a patient for imaging purposes.

As previously noted, the first end 31 of securing member 25 typically extends a greater distance beyond the longitudinal axis 35 of the post member 23 relative to the extension of the second end 33 of the securing member 25 beyond axis 35 (FIGS. 4 and 5), and the first end 27 of the post member 23 is typically wider than the second end 29 of the post member 23, and these structural features/configurations of receiver member 17 further ensure that surgical device 19 is appropriately releasably secured or attached to receiver member 17 (i.e., that end effectors 37, 39 are appropriately releasably secured or attached to the left and right sides 36, 38 of securing member 25). In other words and as depicted in FIGS. 9-13, since the user-operable surgical device 19 typically approaches the assembly 11 from the proximal end 18 of the housing 14 (FIGS. 9-11), the configuration of having the second end 33 of the securing member 25 being not as laterally wide as the first end 31 allows the opened first and second end effectors 37, 39 (which are typically "V" shaped when opened) to quickly and easily be manipulated/positioned around the securing member 25 in order to ensure that surgical device 19 is appropriately releasably secured or attached to receiver member 17 (FIGS. 12-13).

Figure 14:
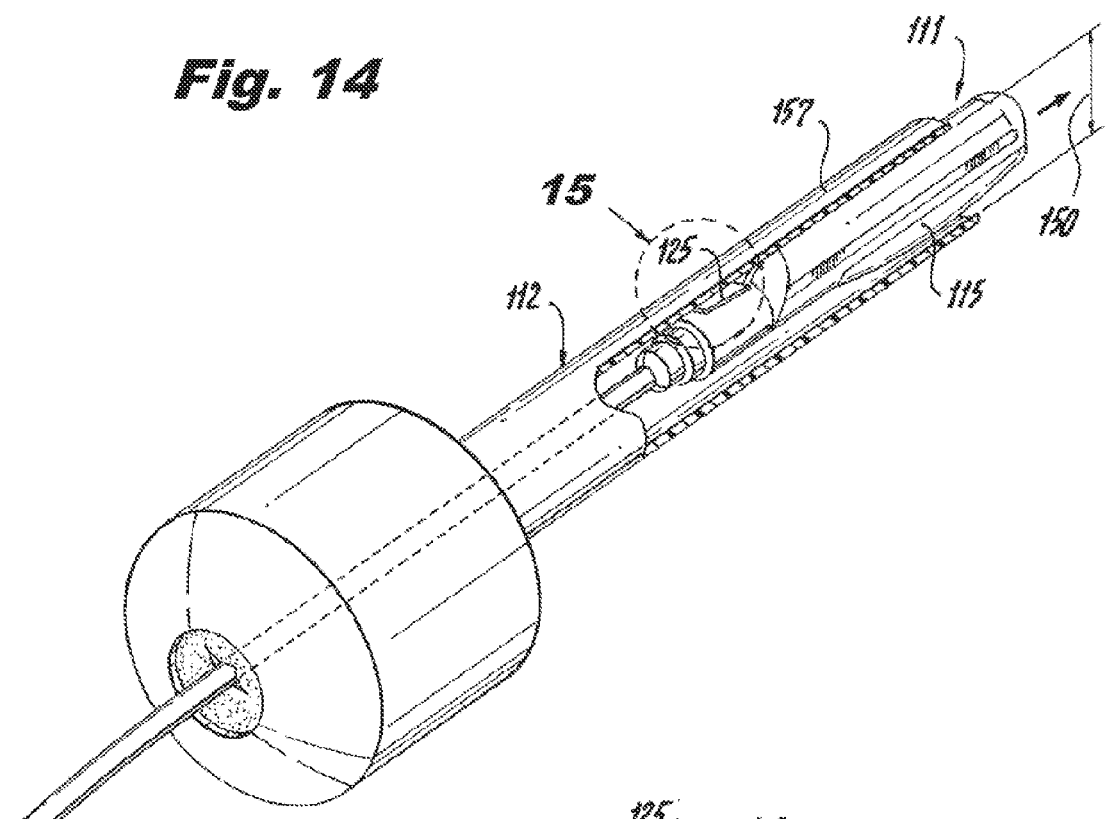
FIG. 14 is a partial sectional side perspective view of an alternative embodiment of an assembly for use in a surgical procedure according to the present disclosure, the assembly positioned within a tool guide.
Figure 15:
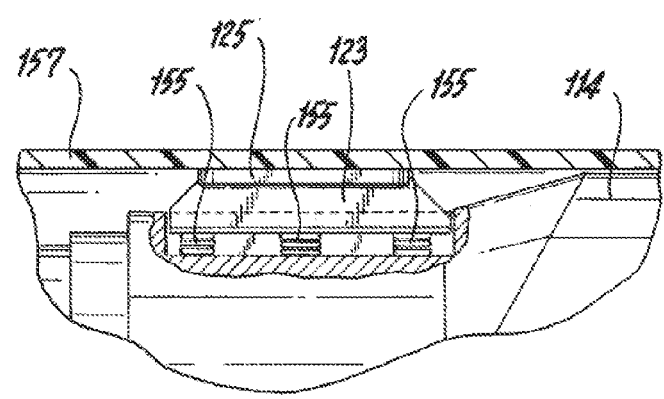
FIG. 15 is an exploded partial sectional side view of the assembly of FIG. 14, the receiver member of the assembly in the retracted position.
Figure 16:
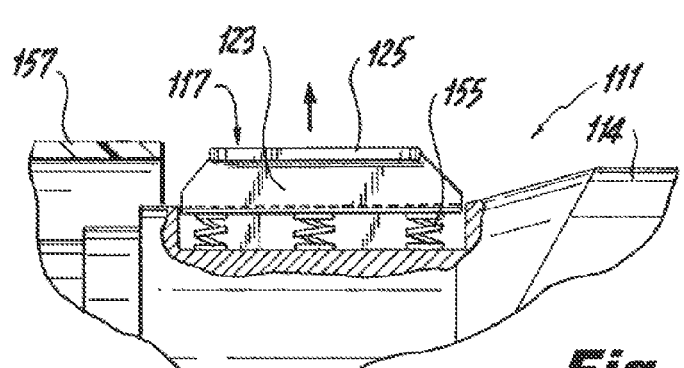
FIG. 16 is an exploded partial sectional side view of the assembly of FIG. 14, the assembly positioned at least partially out of the tool guide, the receiver member of the assembly in the un-retracted position.

In an alternative embodiment and as shown in FIGS. 14-16, the receiver member 117 of assembly 111 is configured and dimensioned to be at least partially retractable within housing 114. For example, when the receiver member 117 is in the retracted position (e.g., at least partially within housing 114—FIGS. 14-15), this thereby allows the assembly 111 to be positioned in and/or inserted through a tool guide 112 having an inner diameter 150 that is substantially the same as or slightly larger than the greatest outer diameter of assembly 111. In other words, the retractable receiver member 117 allows assembly 111 to have a sleeker profile when inserted to the surgical site via tool guide 112 (FIGS. 14-15). Thus, after insertion of assembly 111 to the desired surgical site with the retracted receiver member 117, the post member 123 of receiver member 117 may then be un-retracted from housing 114 to then allow a surgical device 19 to be releasably secured to assembly 111 (e.g., to utilize imaging member 115 for imaging purposes, as similarly discussed above in relation to assembly 11).

In one embodiment and as depicted in FIGS. 14-15, post member 123 of receiver member 117 may be configured/dimensioned to be at least partially retractable within housing 114 via at least one spring member 155. When assembly 111 is inserted into tool guide 112, the inner wall 157 of tool guide 112 pushes against securing member 125, which thereby compresses spring members 155, which in turn allows at least a portion of post member 123 to be retracted within housing 114. It is noted that receiver member 117 and/or spring members 155 may be configured and dimensioned to allow the entire post member 123 (and securing member 125) to be retracted within housing 114 during insertion through tool guide 112. As shown in FIG. 16, when the securing member 125 is positioned out of the tool guide 112, the spring members 155 un-compress, thereby un-retracting the receiver member 117 from its position from inside the housing 114.

In another embodiment and as shown in FIGS. 19-20, post member 223 of receiver member 217 includes a movable sealing member 275, and post member 223 is configured/dimensioned to be at least partially retractable within fluidic chamber 259 of housing 214. In general, fluidic chamber 259 is a fluid-tight compartment (e.g., in conjunction with movable sealing member 275) that is configured and dimensioned to house and/or contain at least one fluid (e.g., when received from fluid line 261). In one embodiment, prior to inserting assembly 211 having receiver member 217 to the desired surgical (e.g. via tool guide 112), a user may force the post member 223 into the retracted position within the fluidic chamber 259 (FIGS. 14 and 19) (e.g., by pushing on securing member 225). Alternatively, it is noted that the inner wall 157 of tool guide 112 may push against securing member 225 to force at least a portion of post member 223 into the fluidic chamber 259. Fluid line 261 is typically in fluid communication with chamber 259 and with an actuating member 251 (e.g., an actuator). When it is desired to have the post member 223 positioned out of the fluidic chamber 259 (FIG. 20), a user may actuate the actuating member 251, which thereby forces fluid into the fluidic chamber 259 via the fluid line 261, which in turn forces post member 223 to its un-retracted position as shown in FIG. 20.

In exemplary embodiments, actuating member 251 is typically located or positioned outside of the body of the patient. Alternatively, actuating member 251 may be positioned on housing 214 or some other location on assembly 211 (e.g., to be actuated via device 19). In one embodiment, post member 223 and securing member 225 are both substantially retracted or housed in housing 214 when the receiver member 217 is in the retracted position.

In another alternative embodiment and as shown in FIGS. 17-18, receiver member 317 (e.g., post member 323) may be configured and dimensioned to be at least partially foldable towards and/or relative to the surface of housing 314 (e.g., to allow assembly 311 to have a sleeker profile when inserted to the surgical site). Thus, after insertion of assembly 311 to the desired surgical site with the folded receiver member 317, the post member 323 of receiver member 317 may then be unfolded away from housing 314 to then allow a surgical device 19 to be releasably secured to assembly 311 as similarly discussed above in relation to assembly 11. Post member 323 may be folded or unfolded via actuating member 351, or manually (e.g., via device 19).

In one embodiment and as shown in FIGS. 17-18, receiver member 317 includes a hinge 397. Hinge 397 is configured and dimensioned to allow receiver member 317 (e.g., post member 323) to be at least partially foldable towards and/or relative to the surface of housing 314.

In one embodiment, prior to inserting assembly 311 having receiver member 317 to the desired surgical (e.g. via tool guide 112), a user may force the post member 323 into the folded position (FIG. 17) (e.g., by pushing on securing member 325). Alternatively, it is noted that the inner wall 157 of tool guide 112 may push against receiver member 317 to force the receiver member into the folded position (and the receiver member may thereby un-fold from the folded position after being positioned out of the tool guide via a spring of hinge 397, or via a user manually, or via actuating means 351, as discussed below).

When it is desired to have the post member 323 un-folded from the folded position, a user may actuate the actuating member 351, which actuates a biasing spring associated with the hinge 397 to force the post member 323 to the un-folded position as shown in FIG. 18.

Turning now to FIGS. 40-42, an alternative assembly 411 may be utilized in conjunction with a user-operable surgical device 219. Assembly 411 may be structurally and functionally similar to the assembly 11 discussed above, with some differences. Moreover, device 219 may be structurally and functionally similar to device 19 discussed above, with some differences.

Similar to assembly 11, the assembly 411 for use in a surgical procedure is typically attached or mounted with respect to a flexible cable 413 or the like. Exemplary assembly 411 takes the form of an imaging assembly (e.g., an ultrasound imaging assembly), although the present disclosure is not limited thereto. Rather, assembly 411 may take a variety of forms to allow a surgeon or technician to extend at least a portion of the assembly 411 to a surgical site for imaging and/or surgical purposes, as discussed above in conjunction with assembly 11.

As shown in FIGS. 40-42, exemplary assembly 411 typically includes housing 414, imaging member 415, and receiver member 417. Similar to receiver member 17, receiver member 417 is typically configured and dimensioned to be releasably secured or attached to a user-operable surgical device 219 (or device 19). As such, a user may then manipulate the user-operable surgical device 219 to thereby move/position the releasably secured assembly 411 to any desired position and/or location (e.g., in a minimally invasive manner within the surgical site for imaging, surgical and/or diagnostic purposes).

In exemplary embodiments, receiver member 417 is a substantially T-shaped or fin-shaped component or protrusion that extends from housing 414 to allow the user operable surgical device 219 to releasably secure or attach to at least a portion of the receiver member 417. The receiver member 417 may also define at least one cavity, recess, channel or receiving feature/surface that allows the user-operable surgical device 219 to releasably secure to assembly 411.

In exemplary embodiments, receiver member 417 includes a post member 423 that extends from housing 414, and a securing member 425 that extends beyond or past both sides of the post member 423 to define a substantially T-shaped or fin-shaped component or protrusion that extends from the housing 414. Post member 423 typically extends from housing 414 a sufficient distance to allow first and second end effectors 237, 239 of device 219 to be positioned and/or attached to post member 423 and underneath securing member 425 when device 219 is releasably attached to receiver member 417, as discussed below.

Similar to receiver member 17, the post member 423 of receiver member 417 has a first end 427 and a second end 429, with the first end 427 typically being wider (e.g., laterally wider) than the second end 429 (e.g., the post member 423 tapers from the first end 427 to the second end 429). The securing member 425 includes a first end 431 and a second end 433. In one embodiment, the first end 431 laterally extends substantially the same distance beyond the longitudinal axis of the post member 423 relative to the lateral extension of the second end 433 of the securing member 425 beyond the longitudinal axis of the post member 423. However, it is noted that similar to receiver member 17, the first end 431 may laterally extend a greater distance beyond the longitudinal axis of the post member 423 relative to the lateral extension of the second end 433 of the securing member 425 beyond the longitudinal axis of the post member 423 (e.g., similar to FIG. 5, with securing member 425 tapering from the first end 431 to the second end 433).

In exemplary embodiments, the user-operable grasper member 219 includes first and second end effectors 237, 239 (e.g., first and second jaws or grasping members 237, 239). Each end effector 237, 239 may or may not include slots (see, e.g., FIGS. 40-42, and FIG. 10). As such, a user may operate the user-operable grasper member 219 (or device 19), either manually or tele-surgically, to open or widen the first and second end effectors 237, 239, and then to position the first and second end effectors 237, 239 adjacent to the left side and right side 437, 439 of post member 423, respectively. The user may then operate the device 219 to then close the end effectors 237, 239 so that at least a portion of the left side 437 of post member 423 is releasably secured to end effector 237, and at least a portion of the right side 439 of post member 423 is releasably secured to end effector 239. Moreover and in this releasably secured position, at least a portion of end effectors 237, 239 is positioned against post member 423 and underneath securing member 425 (FIG. 42). Stated another way, at least a portion of end effectors 237, 239 are positioned underneath securing member 425 after the end effectors 237, 239 are releasably secured to post member 423.

In this way, user-operable surgical device 219 is now releasably secured or attached to receiver member 417 of assembly 411, and a user may then move/position the assembly 411 to any desired position and/or location (e.g., for imaging/surgical purposes) by operating device 219 (e.g., either manually or tele-surgically).

It is to be noted that receiver member 417 of assembly 411 may be configured and dimensioned to operate structurally and functionally similar to: (i) the receiver member 117 of assembly 111 (e.g., to be at least partially retractable within housing 414, as similarly depicted in FIGS. 14-16), (ii) the receiver member 317 of assembly 311 (e.g., to be at least partially foldable towards and/or relative to the surface of housing 414, as similarly depicted in FIGS. 17-18), or (iii) the receiver member 217 of assembly 211 (e.g., to be at least partially retractable within a fluidic chamber of housing 414, as similarly depicted in FIGS. 19-20).

Moreover, it is also to be noted that post member 423 of receiver member 417 may include at least one projection or protrusion that is configured and dimensioned to operate in a structurally and functionally similar fashion to projections or protrusions 537c, 539c, 537d or 539d as disclosed and described below in conjunction with FIGS. 34-35 and FIGS. 38-39.

Furthermore, it is also to be noted that post member 423 of receiver member 417 may include at least one surface that is configured and dimensioned to operate in a structurally and functionally similar fashion to surfaces 537a, 539a, 537b or 539b as disclosed and described below in conjunction with FIGS. 32-33 and FIGS. 36-36A.

Turning now to FIGS. 21-39, an alternative assembly 511 may be utilized in conjunction with a user-operable surgical device 319 (or device 19, or device 219, etc.). Assembly 511 may be structurally and functionally similar to the assembly 11 discussed above, with some differences. Moreover, device 319 may be structurally and functionally similar to device 19 discussed above, with some differences.

Similar to assembly 11, the assembly 511 for use in a surgical procedure is typically attached or mounted with respect to a flexible cable 513 or the like. Exemplary assembly 511 takes the form of an imaging assembly (e.g., an ultrasound imaging assembly), although the present disclosure is not limited thereto. Rather, assembly 511 may take a variety of forms to allow a surgeon or technician to extend at least a portion of the assembly 511 to a surgical site for imaging and/or surgical purposes, as discussed above in conjunction with assembly 11.

As shown in FIGS. 21-22, exemplary assembly 511 typically includes housing 514, imaging member 515, and receiver member 517. Similar to receiver member 17, receiver member 517 is typically configured and dimensioned to be releasably secured or attached to a user-operable surgical device 319 (or device 19, or device 219, etc.). As such, a user may then manipulate the user-operable surgical device 319 to thereby move/position the releasably secured assembly 511 to any desired position and/or location (e.g., in a minimally invasive manner within the surgical site for imaging, surgical and/or diagnostic purposes).

In exemplary embodiments, receiver member 517 is a component or protrusion that extends from housing 514 to allow the user operable surgical device 319 to releasably secure or attach to at least a portion of the receiver member 517. The receiver member 517 may also define at least one receiving feature and/or surface that allows the user-operable surgical device 319 to releasably secure to assembly 511.

In exemplary embodiments, receiver member 517 includes a post member 523 that extends from housing 514. Post member 523 typically extends from housing 514 a sufficient distance to allow at least a portion of first and second end effectors 337, 339 of device 319 to be positioned adjacent and/or attached/secured to at least a portion of post member 523 when device 319 is releasably attached or secured to receiver member 517, as discussed below.

Similar to receiver member 17, the post member 523 of receiver member 517 has a first end 527 and a second end 529, with the first end 527 typically being wider (e.g., laterally wider) than the second end 529 (e.g., the post member 523 tapers from the first end 527 to the second end 529). Post member 523 may also include an attachment member 524, the attachment member 524 being configured and dimensioned to be attached, secured or mounted with respect to the housing 514 (e.g., with respect to a groove or slot of housing 514) of the assembly 511.

Figure 30:
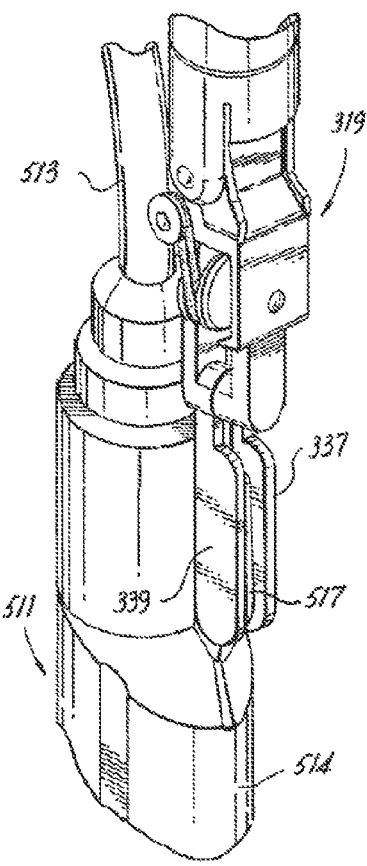
FIG. 30 is a partial side perspective view of the assembly of FIG. 21 with a user-operable surgical device attached thereto.

In exemplary embodiments, the user-operable grasper member 319 includes first and second end effectors 337, 339 (e.g., first and second jaws or grasping members 337, 339). Each end effector 337, 339 may or may not include slots. As such, a user may operate the user-operable grasper member 319 (or device 19 or 219), either manually or tele-surgically, to open or widen the first and second end effectors 337, 339, and then to position the first and second end effectors 337, 339 adjacent to the left side and right side 537, 539 of post member 523, respectively. The user may then operate the device 319 to then close the end effectors 337, 339 so that at least a portion of the left side 537 of post member 523 is releasably secured to end effector 337, and at least a portion of the right side 539 of post member 523 is releasably secured to end effector 339 (FIG. 30). In this releasably secured position, at least a portion of end effectors 337, 339 are positioned against at least a portion of post member 523.

Figure 31:
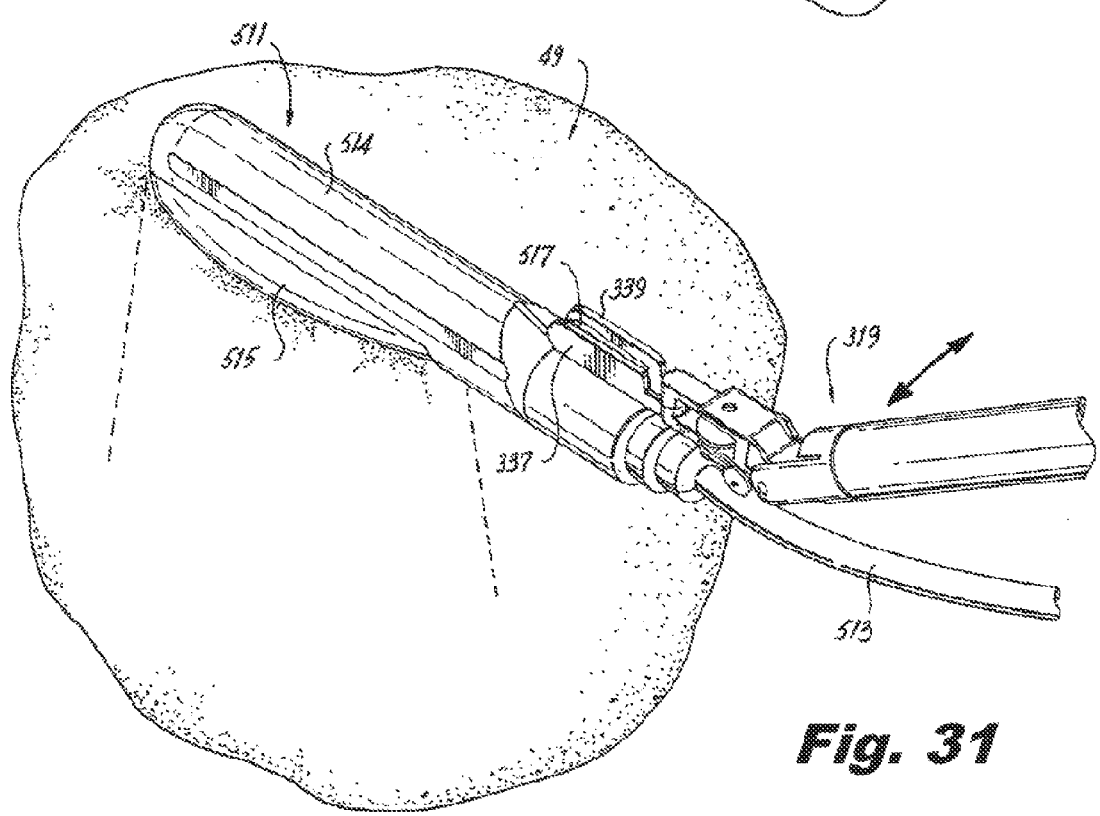
FIG. 31 is an in situ side perspective view of the assembly of FIG. 21 with a user-operable surgical device attached thereto.

In this way, user-operable surgical device 319 is now releasably secured or attached to receiver member 517 of assembly 511, and a user may then move/position the assembly 511 to any desired position and/or location (e.g., for imaging/surgical purposes) by operating device 319 (e.g., either manually or tele-surgically). For example and as shown in FIG. 31, a user may then move and/or position the assembly 511 over, across and/or adjacent to at least a portion of tissue or organ 49 of a patient for imaging/surgical purposes.

It is to be noted that prior to releasably securing device 319 to receiver member 517, the device 319 may approach receiver member 517 from a variety of angles/positions. For example and as shown in FIGS. 27, 28 and 30, the device 319 may approach assembly 511 from the proximal end of assembly 511. Alternatively and as shown in FIG. 29, device 319 may approach receiver member 517 of assembly 511 from a different position (e.g., from a position located above the receiver member 517) so that at least a portion of end effectors 337, 339 are positioned against at least a portion of post member 523 once device 319 is releasably secured to receiver member 517. In one embodiment and as depicted in FIGS. 37 and 37A, receiver member 517' includes a post member 523' that is slightly tapered from the bottom side 585' to the top side 587' to facilitate the releasable securement of device 319 to receiver member 517' from a variety of angles/positions (e.g., from a position located above the receiver member 517 as shown in FIG. 29). Stated another way, the width D of the post member 523' at the bottom side 585' is larger than the width d of the post member 523' at the top side 587' to facilitate the releasable securement of device 319 to receiver member 517' from a variety of angles/positions.

As previously noted, the first end 527 of the post member 523 is typically wider than the second end 529 of the post member 523, and this structural feature/configuration of receiver member 517 further ensures that surgical device 319 is appropriately releasably secured or attached to receiver member 517 (e.g., that end effectors 337, 339 are appropriately releasably secured or attached to the left and right sides 537, 539 of post member 523).

Figure 32:
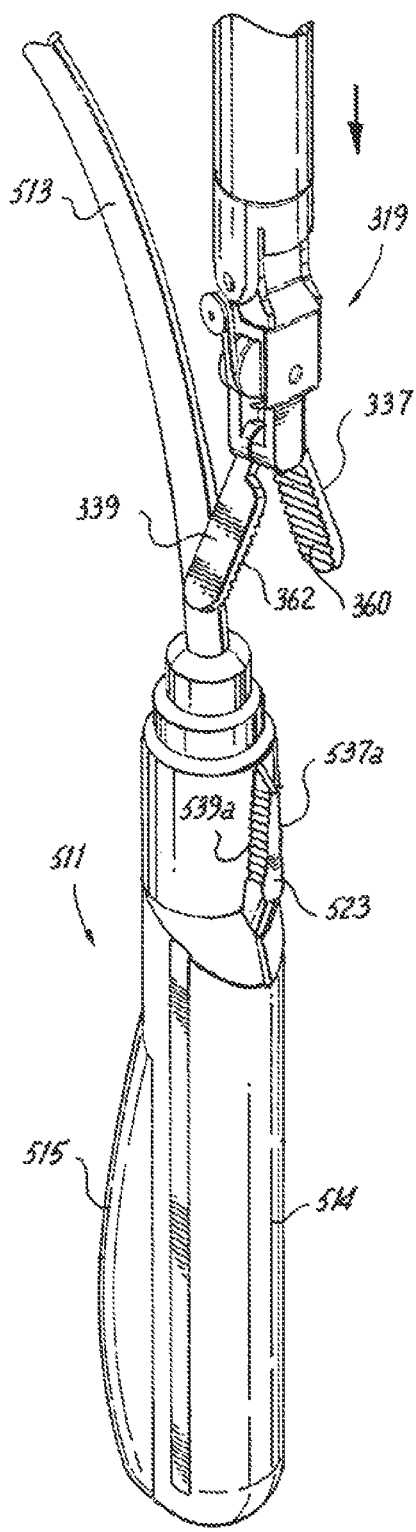
FIGS. 32-33 are side perspective views of another exemplary assembly for use in a surgical procedure, along with a user-operable surgical device, prior to attachment thereto.
Figure 33:
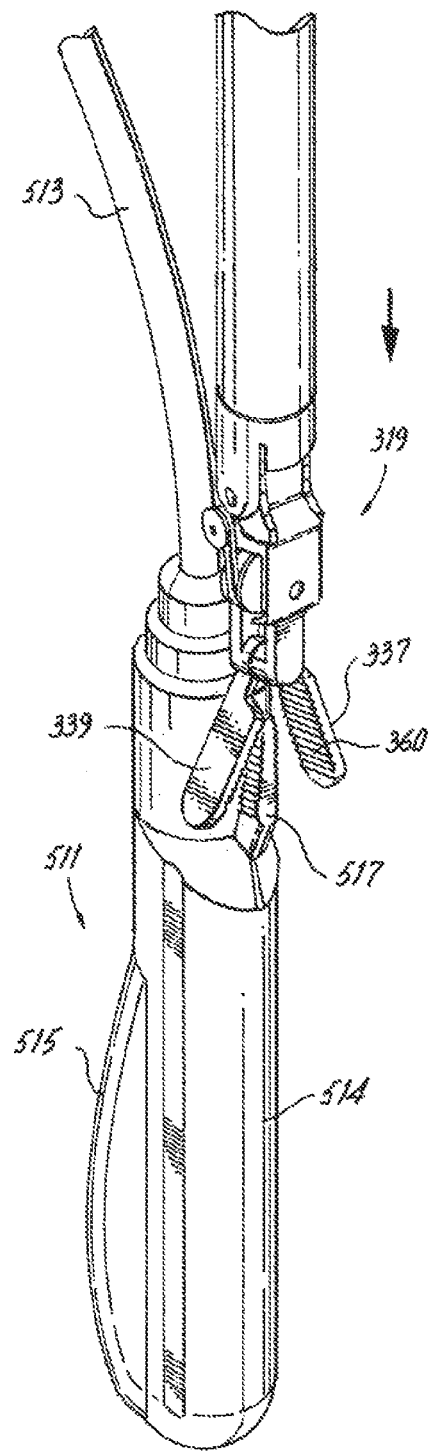

In one embodiment and as depicted in FIGS. 32-33, end effectors 337, 339 include grooved interior surfaces 360, 362, and at least a portion of left side and right side 537, 539 of post member 523 includes grooved exterior surfaces 537a, 539a. As such, a user may then operate the device 319 to close the end effectors 337, 339 so that at least a portion of the left side grooved exterior surface 537a of post member 523 is releasably secured to grooved interior surface 360 of end effector 337, and at least a portion of the right side grooved exterior surface 539a of post member 523 is releasably secured to grooved interior surface 362 of end effector 339.

In another embodiment and as depicted in FIGS. 36 and 36A, at least a portion of left side and right side 537, 539 of post member 523 includes roughened or textured exterior surfaces 537b, 539b. As such, a user may then operate the device 319 to close the end effectors 337, 339 so that at least a portion of the left side roughened/textured exterior surface 537b of post member 523 is releasably secured to end effector 337, and at least a portion of the right side roughened/textured exterior surface 539b of post member 523 is releasably secured to end effector 339.

Figure 34:
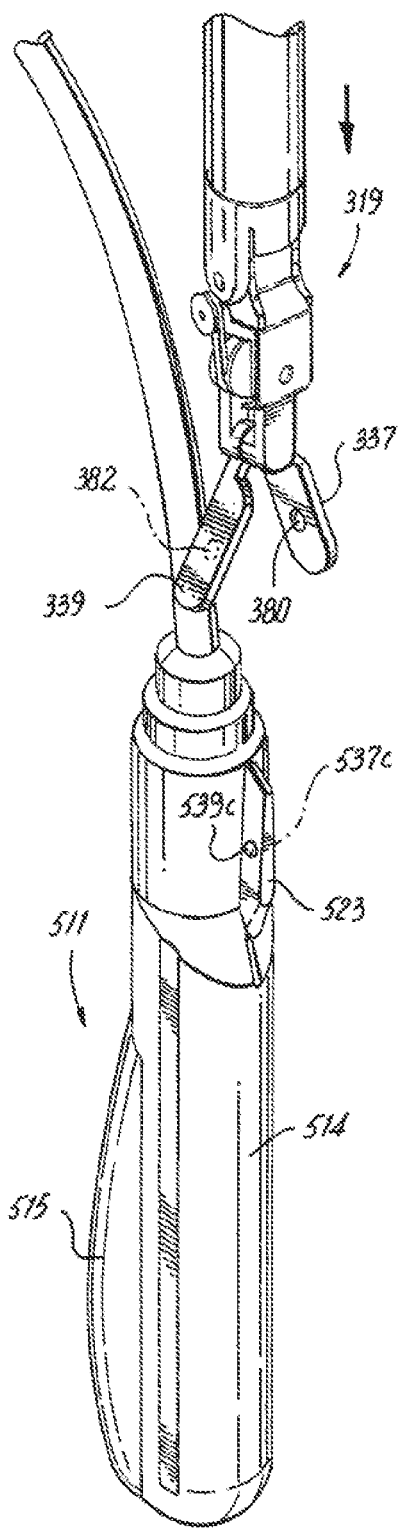
FIGS. 34-35 are side perspective views of another exemplary assembly for use in a surgical procedure, along with a user-operable surgical device, prior to attachment thereto.
Figure 35:
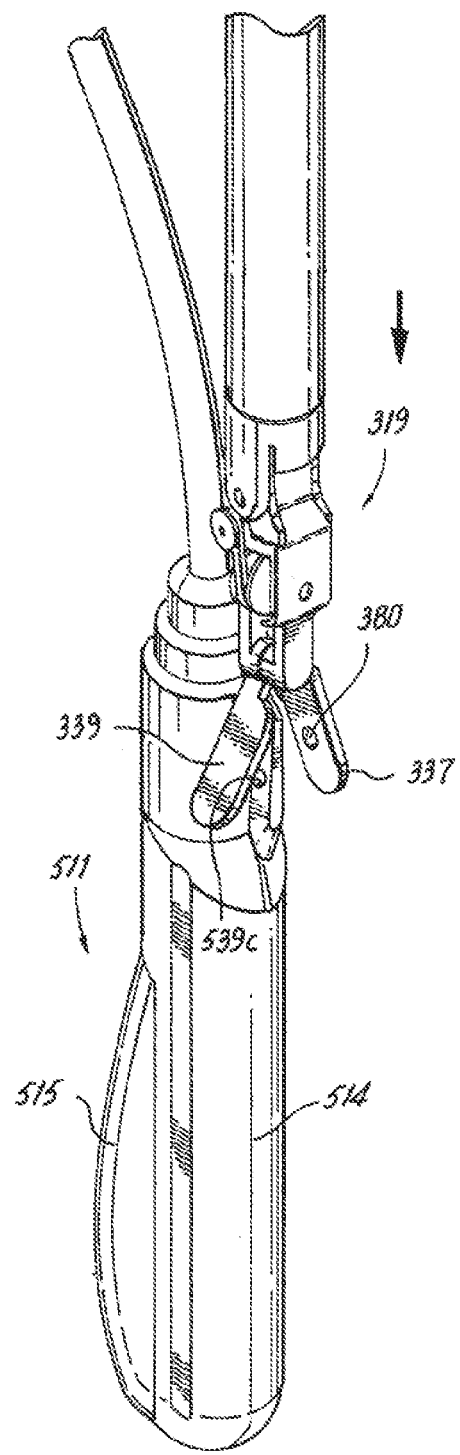

In another embodiment and as depicted in FIGS. 34-35, end effectors 337, 339 include an interior recess or aperture 380, 382, and left side and right side 537, 539 of post member 523 includes protrusions or knobs 537c, 539c. As such, a user may then operate the device 319 to close the end effectors 337, 339 so that left side knob 537c of left side 537 is releasably positioned and/or secured within at least a portion of recess/aperture 380 of end effector 337, and so that right side knob 539c of right side 539 is releasably positioned and/or secured within at least a portion of recess/aperture 382 of end effector 339.

Figure 38:
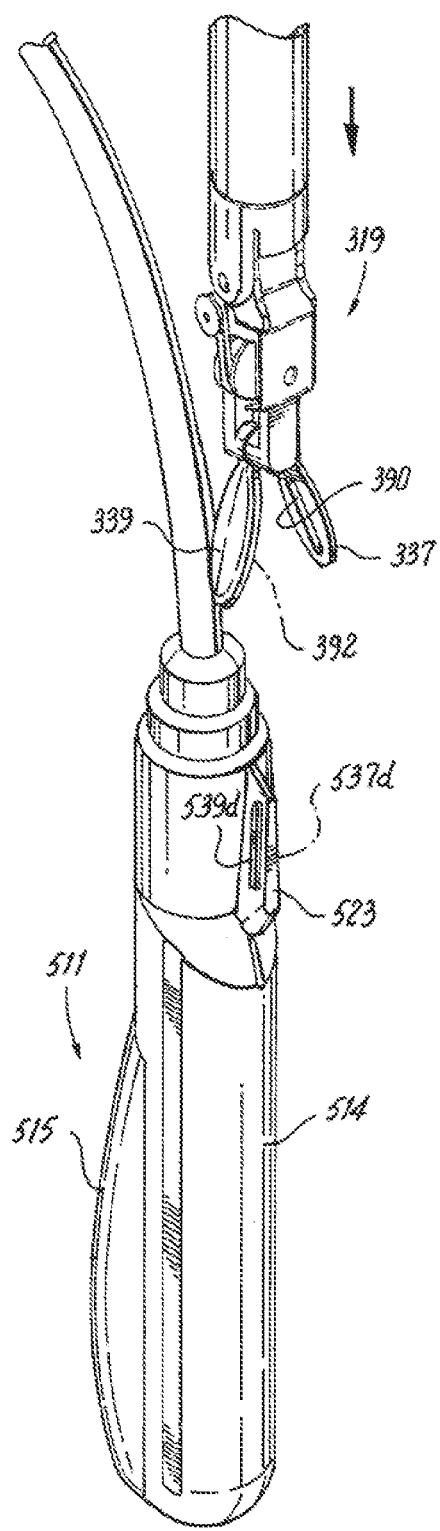
FIGS. 38-39 are side perspective views of another exemplary assembly for use in a surgical procedure, along with a user-operable surgical device, prior to attachment thereto.
Figure 39:
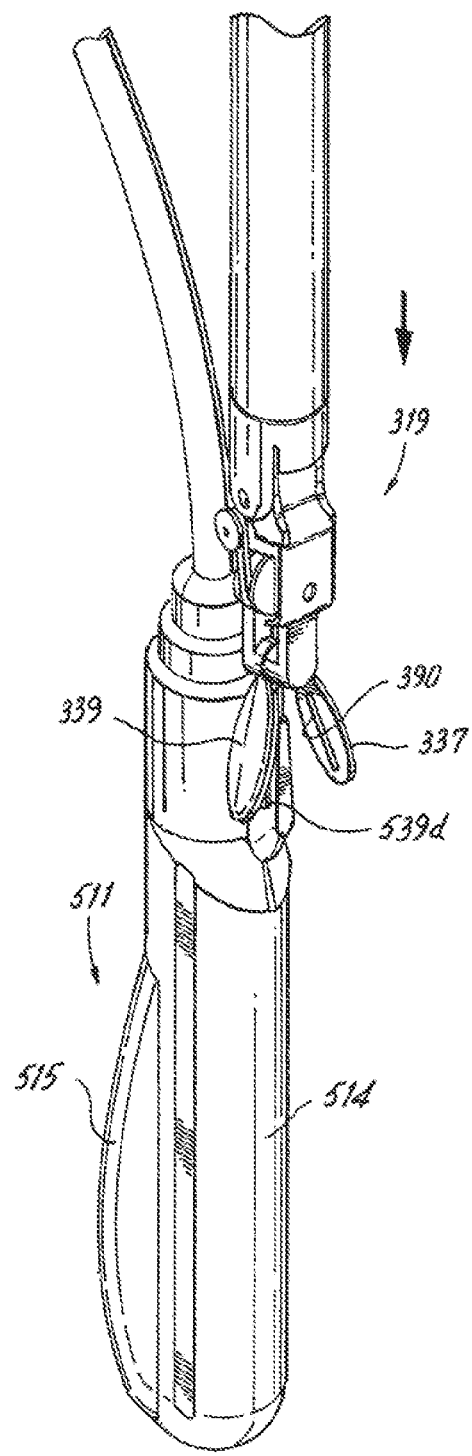

In another embodiment and as depicted in FIGS. 38-39, end effectors 337, 339 include an interior concave or cup-like portion 390, 392, and left side and right side 537, 539 of post member 523 includes protrusions or extending members 537d, 539d. As such, a user may then operate the device 319 to close the end effectors 337, 339 so that left side extending member 537d of left side 537 is releasably positioned and/or secured within at least a portion of concave or cup-like portion 390 of end effector 337, and so that right side extending member 539d of right side 539 is releasably positioned and/or secured within at least a portion of concave or cup-like portion 392 of end effector 339.

It is to be noted that receiver member 517 of assembly 511 may be configured and dimensioned to operate structurally and functionally similar to: (i) the receiver member 117 of assembly 111 (e.g., to be at least partially retractable within housing 514, as similarly depicted in FIGS. 14-16), (ii) the receiver member 317 of assembly 311 (e.g., to be at least partially foldable towards and/or relative to the surface of housing 514, as similarly depicted in FIGS. 17-18), or (iii) the receiver member 217 of assembly 211 (e.g., to be at least partially retractable within a fluidic chamber of housing 514, as similarly depicted in FIGS. 19-20).

As previously noted and in certain embodiments, the receiver member may be releasably and/or detachably securable to the housing of the assembly for use in a surgical procedure (e.g., releasably/detachably securable to the surgical/imaging assembly housing). For example and as shown in FIGS. 43-59, the receiver member 717 (or 817) may be releasably and/or detachably securable to the housing 714 (or 914) of the assembly 711 (or 911) for use in a surgical procedure.

In exemplary embodiments and as shown in FIGS. 43-51, an alternative assembly 711 and receiver member 717 may be utilized in conjunction with a user-operable surgical device 719. Assembly 711 may be structurally and functionally similar to the assembly 11 discussed above, with some differences. Moreover, device 719 may be structurally and functionally similar to device 19 discussed above, with some differences.

Similar to assembly 11, the assembly 711 for use in a surgical procedure is typically attached or mounted with respect to a flexible cable 713 or the like. Exemplary assembly 711 takes the form of an imaging assembly (e.g., an ultrasound imaging assembly), although the present disclosure is not limited thereto. Rather, assembly 711 may take a variety of forms to allow a surgeon or technician to extend at least a portion of the assembly 711 to a surgical site for imaging and/or surgical purposes, as discussed above in conjunction with assembly 11.

As shown in FIGS. 43-51, exemplary assembly 711 typically includes housing 714, imaging member 715, and receiver member 717. Similar to receiver member 17 (and after the receiver member 717 is releasably secured or attached to housing 714—discussed below), receiver member 717 is typically configured and dimensioned to be releasably secured or attached to a user-operable surgical device 719 (or device 19). As such, a user may then manipulate the user-operable surgical device 719 to thereby move/position the releasably secured assembly 711 to any desired position and/or location (e.g., in a minimally invasive manner within the surgical site for imaging, surgical and/or diagnostic purposes).

In exemplary embodiments, the receiver member 717 includes an attachment section 774, a post member 723 and a securing member 725. The post member 723 typically extends from the attachment section 774 (e.g., from the top side 778 of attachment section 774), and the securing member typically extends past both sides of the post member 723 to define a substantially T-shaped or fin-shaped portion of the receiver member 717. In general, the substantially T-shaped or fin-shaped component or protrusion that extends from the attachment section 774 allows the user operable surgical device 719 to releasably secure or attach to at least a portion of the receiver member 717, once the receiver member 717 is releasably secured or attached to housing 714 (discussed further below). It is noted that the receiver member 717 may also define at least one cavity, recess, channel or receiving feature/surface that allows the user-operable surgical device 719 to releasably secure to assembly 711.

Figure 46:
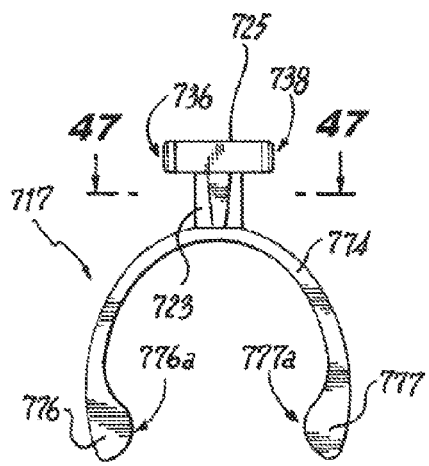
FIG. 46 is a proximal end view of the receiver member of FIG. 45.
Figure 47:
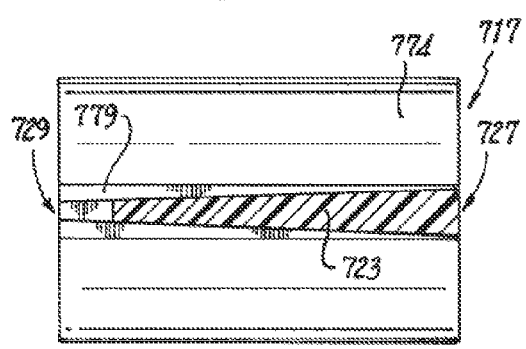
FIG. 47 is a top cross-sectional view of the receiver member of FIG. 45, taken substantially along the lines 47-47 of FIG. 46.

In exemplary embodiments and as shown in FIGS. 43-51, the attachment section 774 is substantially U-shaped or C-shaped, and typically extends from a first end 776 to a second end 777 to define the substantially U-shaped or C-shaped attachment section 774. First and second ends 776, 777 typically include inner portions 776a and 777a that extend inwardly toward the center of the attachment section 774 (FIG. 46). As noted, post member 723 typically extends from the top side 778 of attachment section 774. In certain embodiments, the top side 778 includes a substantially planar section or region 779 from which the post member 723 extends.

Figures 43, 44:
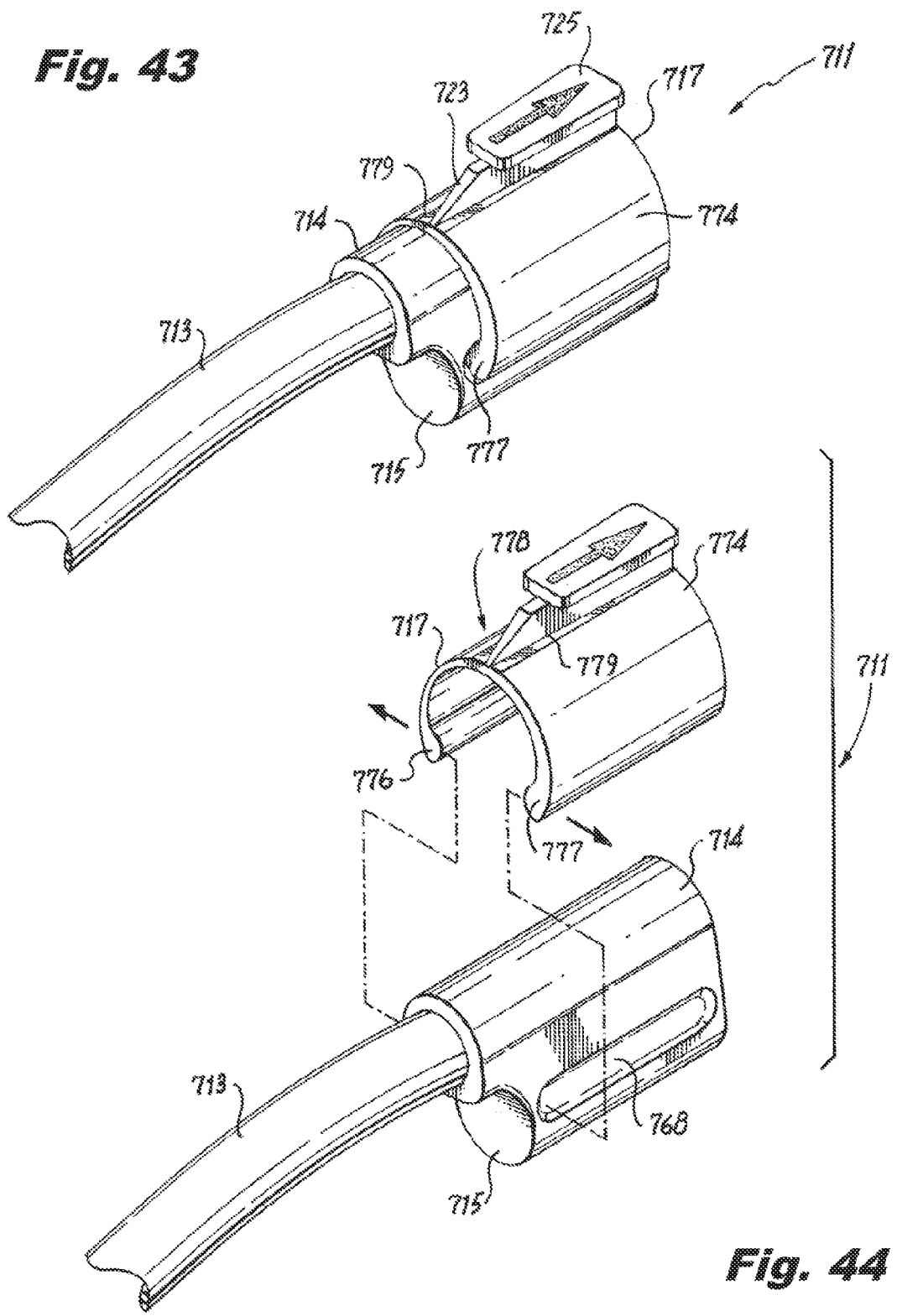
FIG. 43 is a side perspective view of another exemplary assembly for use in a surgical procedure.
FIG. 44 is a side perspective view of the assembly of FIG. 43, prior to attachment of the receiver member.
Figure 45:
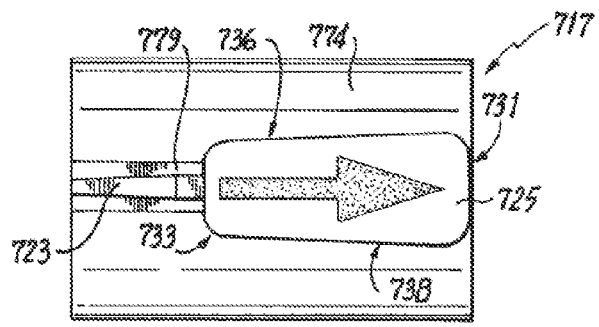
FIG. 45 is a top view of the receiver member of the assembly of FIG. 43.
Figure 51:
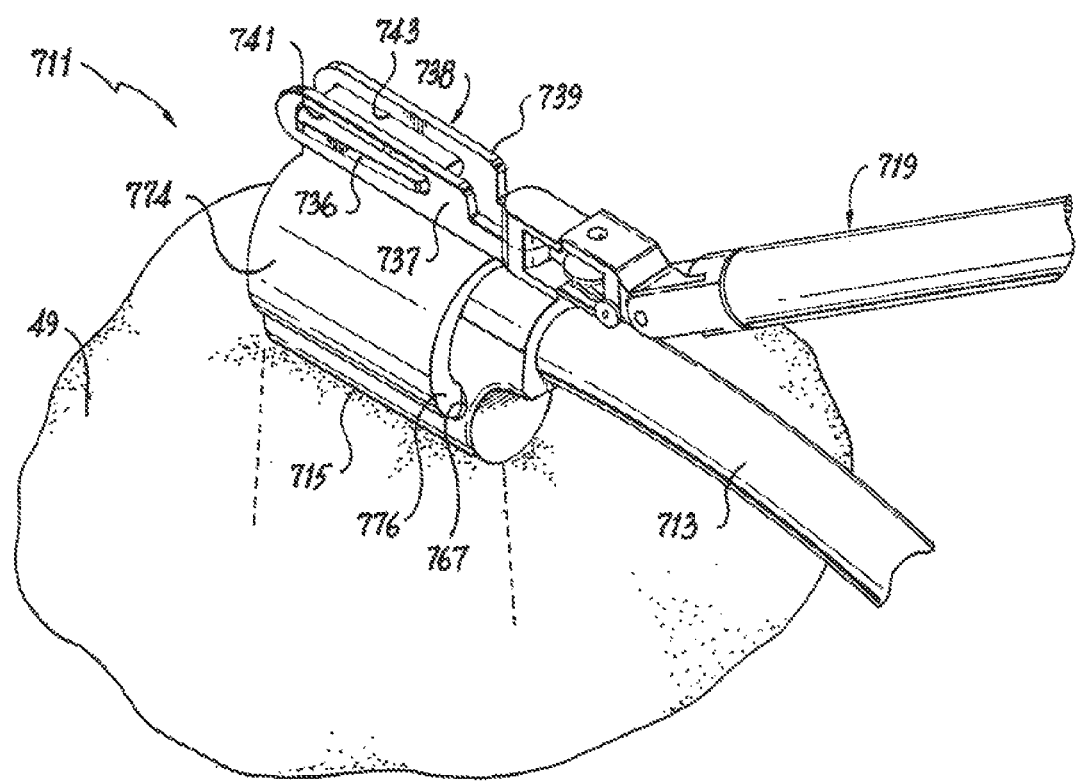
FIG. 51 is an in situ side perspective view of the assembly of FIG. 43 with an exemplary user-operable surgical device attached thereto.
Figure 52:
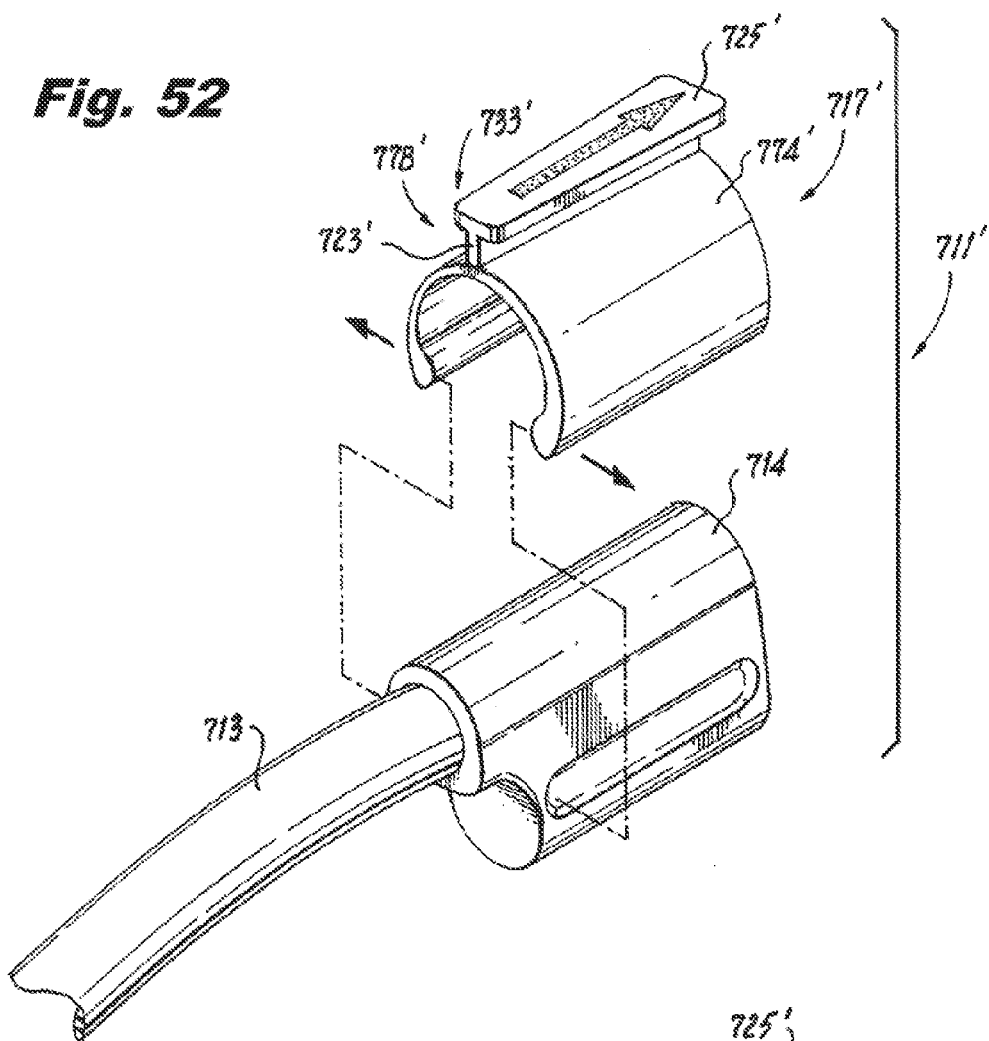
FIG. 52 is a side perspective view of another exemplary assembly for use in a surgical procedure, prior to attachment of the receiver member.
Figure 53:
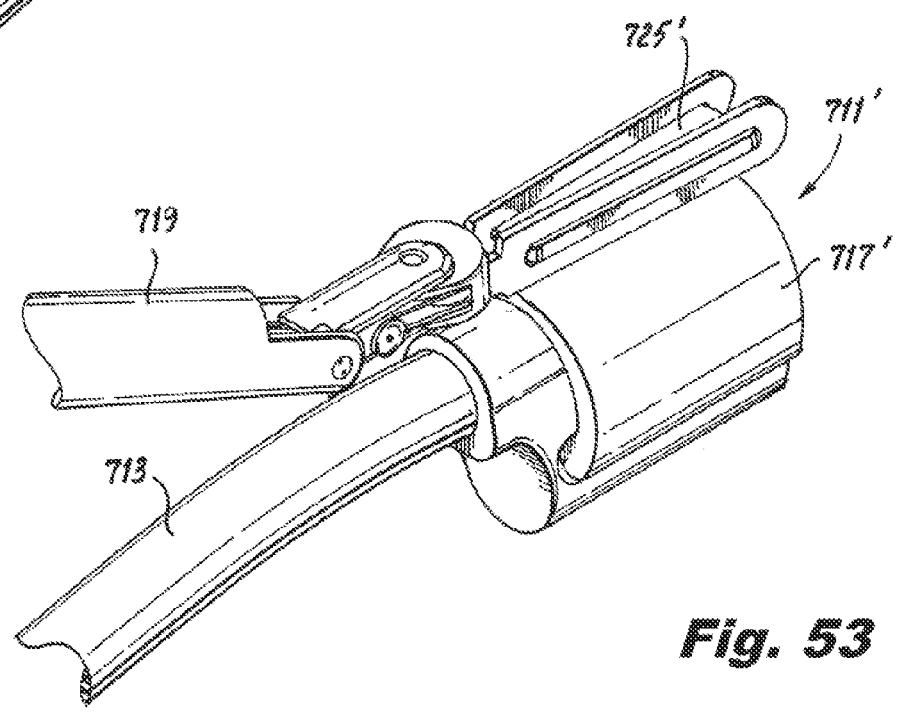
FIG. 53 is a side perspective view of the assembly of FIG. 52 with an exemplary user-operable surgical device attached thereto.

Housing 714 of assembly 711 typically includes at least one first groove or recess 767, and at least one second groove or recess 768 (FIGS. 44 and 51). In general, first groove 767 is configured and dimensioned to allow at least a portion of the first end 776 (e.g., inner portion 776a) of the attachment section 774 to be releasably positioned within at least a portion of first groove 767, and second groove 768 is configured and dimensioned to allow at least a portion of the second end 777 (e.g., inner portion 777a) of the attachment section 774 to be releasably positioned within at least a portion of second groove 768, in order to releasably secure or attach the receiver member 717 to housing 714 (FIG. 44).

In exemplary embodiments and as depicted in FIG. 44, the first and second ends 776, 777 of the attachment section 774 are configured and dimensioned to flex, bend or expand outwardly when the attachment section 774 is positioned around the housing 714 until at least a portion of first and second ends 776, 777 are positioned within first and second grooves 767, 768, respectively, to releasably secure/attach the attachment section 774 to housing 714 (e.g., in a snap-on or clip-on fashion or manner). In short, attachment section 774 is configured to releasably clip-on or snap on to housing 714, with ends 776, 777 flexing outwardly over housing 714 until the ends are positioned within grooves 767, 768, respectively. In this manner, attachment section 774 may be releasably secured or attached to housing 714 of assembly 711. Thereafter and as noted, receiver member 717 is typically configured and dimensioned to be releasably secured or attached to a user-operable surgical device 719. As such, a user may then manipulate the user-operable surgical device 719 to thereby move/position the releasably secured assembly 711 to any desired position and/or location (e.g., in a minimally invasive manner within the surgical site for imaging, surgical and/or diagnostic purposes) (FIG. 51).

However, it is to be noted that other portions/sections and/or structures/features (e.g., knobs, protrusions, etc.) of first and second ends 776, 777 and/or of attachment section 774 may be configured and dimensioned to be positioned within grooves 767, 768 other than inner portions 776a, 777a to releasably secure attachment section 774 and receiver member 717 to housing 714 (or 914—discussed below).

Figure 49:
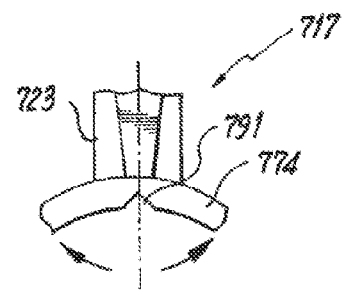
FIG. 49 is a partial proximal end view of the receiver member of FIG. 48.
Figure 48:
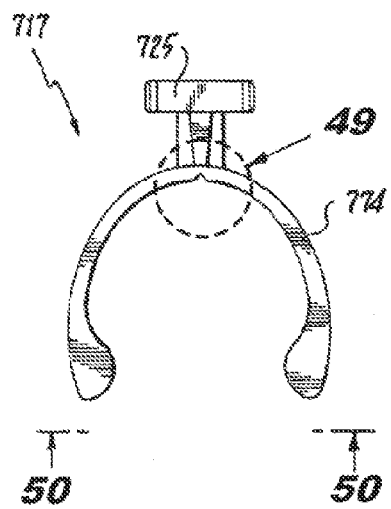
FIG. 48 is a proximal end view of another exemplary receiver member of the present disclosure.
Figure 50:
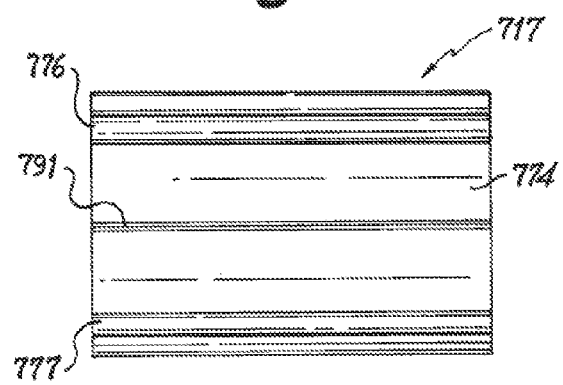
FIG. 50 is a bottom view of the receiver member of FIG. 48.

In certain embodiments and as shown in FIGS. 48-50, attachment section 774 may include a hinge 791 or the like (e.g., a living hinge). Hinge 791 typically extends at least partially underneath the top side 778 of section 774. In exemplary embodiments, hinge 791 extends underneath the top side 778 and underneath post member 723. Hinge 791 typically is configured and dimensioned to facilitate the ends 776, 777 of the attachment section 774 to flex or extend outwardly when the attachment section 774 is placed over the housing 714.

As noted, the post member 723 typically extends from the attachment section 774, and the securing member 725 typically extends past both sides of the post member 723 to define a substantially T-shaped or fin-shaped portion of the receiver member 717. After the receiver member 717 is releasably secured or attached to housing 714, the substantially T-shaped or fin-shaped component or protrusion that extends from the attachment section 774 allows the user operable surgical device 719 to releasably secure or attach to at least a portion of the receiver member 717.

For example, a user may operate the user-operable grasper member 719 (e.g., either manually or tele-surgically) to firstly open or widen the first and second end effectors 737, 739, and then secondly to position the slots 741, 743 of grasper member 719 adjacent to the left side and right side 736, 738 of securing member 725, respectively. The user may then operate the grasper member 719 to then close the end effectors 737, 739 so that at least a portion of the left side 736 of securing member 725 is releasably secured within slot 741, and at least a portion of the right side 738 of securing member 725 is releasably secured within slot 743 (FIG. 51). In exemplary embodiments, at least a portion of left side 736 extends through slot 741 and at least a portion of right side 738 extends through slot 743 after the end effectors 737, 739 are releasably secured to receiver member 717.

In this way, user-operable surgical device 719 is now releasably secured or attached to receiver member 717 of assembly 711, and a user may then move/position the assembly 711 to any desired position and/or location (e.g., for imaging/surgical purposes) by operating device 719 (e.g., either manually or tele-surgically). For example and as shown in FIG. 51, a user may then move and/or position the assembly 711 over, across and/or adjacent to at least a portion of tissue or organ 49 of a patient for imaging purposes.

It is also to be noted that post member 723 may also extend from attachment section 774 a sufficient distance to allow first and second end effectors 737, 739 of device 719 (or device 219, etc.) to be positioned and/or attached to post member 723 and underneath securing member 725 when device 719 is releasably attached to receiver member 717, as similarly discussed above in connection with FIGS. 40-42.

Similar to receiver member 17, the post member 723 of receiver member 717 has a first end 727 and a second end 729, with the first end 727 typically being wider (e.g., laterally wider) than the second end 729 (e.g., the post member 723 tapers from the first end 727 to the second end 729). The securing member 725 includes a first end 731 and a second end 733. The first end 731 typically laterally extends a greater distance beyond the longitudinal axis of the post member 723 relative to the lateral extension of the second end 733 of the securing member 725 beyond the longitudinal axis of the post member 723 (e.g., the securing member 725 tapers from the first end 731 to the second end 733). In exemplary embodiments, these structural features/configurations of receiver member 717 further ensure that surgical device 719 is appropriately releasably secured or attached to receiver member 717 (i.e., that end effectors 737, 739 are appropriately releasably secured or attached to the left and right sides 736, 738 of securing member 725). In other words and as depicted in FIG. 51, since the user-operable surgical device 719 typically approaches the assembly 711 from the proximal end of the housing 714, the configuration of having the second end 733 of the securing member 725 being not as laterally wide as the first end 731 allows the opened first and second end effectors 737, 739 (which are typically "V" shaped when opened) to quickly and easily be manipulated/positioned around the securing member 725 in order to ensure that surgical device 719 is appropriately releasably secured or attached to receiver member 717.

However, it is noted that the first end 731 may laterally extend substantially the same distance beyond the longitudinal axis of the post member 723 relative to the lateral extension of the second end 733 of the securing member 725 beyond the longitudinal axis of the post member 723. It is also noted that in certain embodiments (FIGS. 43-51), the second end 733 of the securing member 725 may not extend proximally to the proximal end of the top side 778 of the attachment section 774 (e.g., may not extend substantially the entire length of top side 778). However, in certain other embodiments of assembly 711' (FIGS. 52-53), the second end 733' of securing member 725' may extend substantially the entire length along the top side 778' of attachment member 774' of receiver member 717' (e.g., substantially above the entire length of post member 723').

It is also to be noted that post member 723 of receiver member 717 may include at least one projection or protrusion that is configured and dimensioned to operate in a structurally and functionally similar fashion to projections or protrusions 537*c*, 539*c*, 537*d* or 539*d* as disclosed and described above in conjunction with FIGS. 34-35 and FIGS. 38-39.

Furthermore, it is also to be noted that post member 723 of receiver member 717 may include at least one surface that is configured and dimensioned to operate in a structurally and functionally similar fashion to surfaces 537*a*, 539*a*, 537*b* or 539*b* as disclosed and described above in conjunction with FIGS. 32-33 and FIGS. 36-36A.

Figure 54:
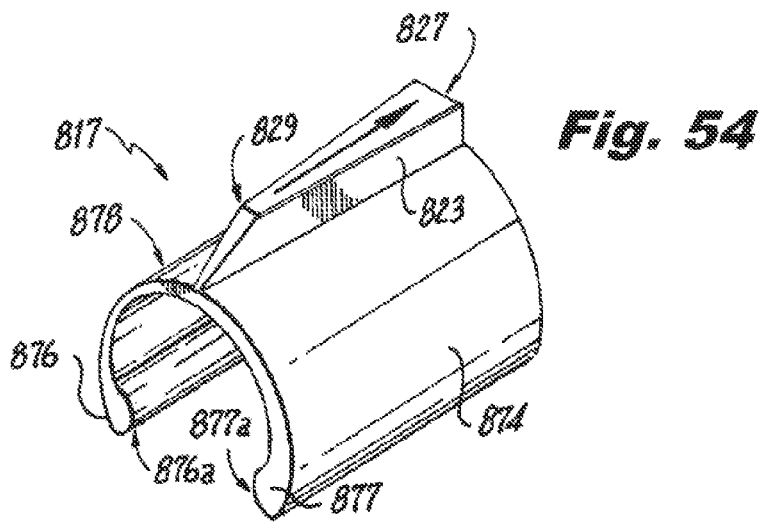
FIGS. 54-56 are side perspective views of other exemplary receiver members for use in surgical procedures.
Figure 55:
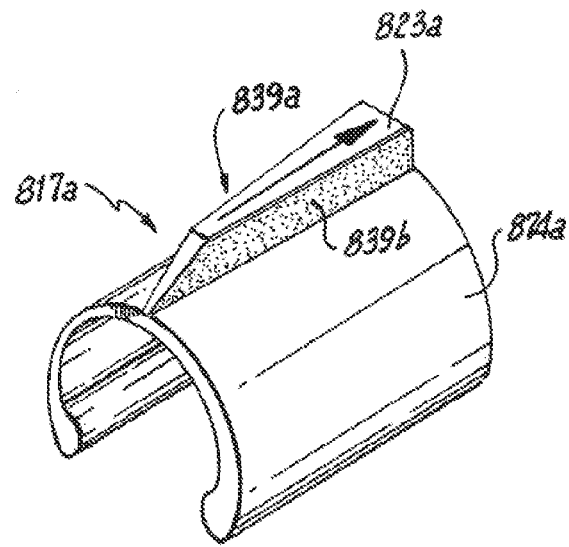
Figure 56:
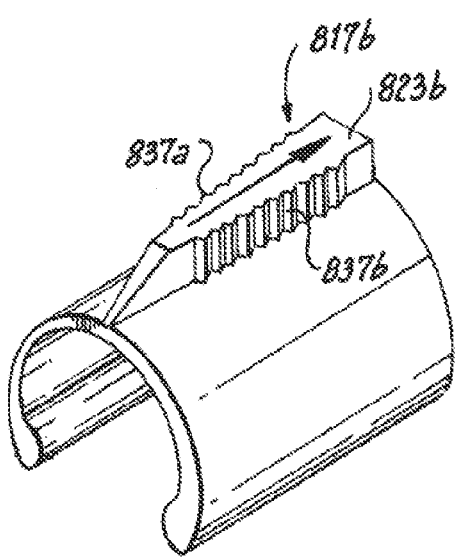

Turning now to FIGS. 54-56, an alternative receiver member 817 (or 817*a*, or 817*b*) may be utilized in conjunction with housing 714 (or housing 914—discussed below), and in conjunction with a user-operable surgical device 719 (or device 319, etc.). Receiver member 817 may be structurally and functionally similar to the receiver member 717 discussed above, with some differences.

Similar to receiver member 17, receiver member 817 is typically configured and dimensioned to be releasably secured or attached to a user-operable surgical device 719 (or device 319, etc.). In exemplary embodiments, receiver member 817 includes a component or protrusion that extends from an attachment section 874 to allow the user operable surgical device 719 to releasably secure or attach to at least a portion of the receiver member 817. The receiver member 817 may also define at least one receiving feature and/or surface that allows the user-operable surgical device 719 to releasably secure to receiver member 817.

In exemplary embodiments, receiver member 817 includes a post member 823 that extends from attachment section 874. Post member 823 typically extends from attachment section 874 a sufficient distance to allow at least a portion of first and second end effectors 737, 739 of device 719 to be positioned adjacent and/or attached/secured to at least a portion of post member 823 when device 719 is releasably attached or secured to receiver member 817, as discussed below.

In exemplary embodiments and as shown in FIG. 54, the attachment section 874 is substantially U-shaped or C-shaped, and typically extends from a first end 876 to a second end 877 to define the substantially U-shaped or C-shaped attachment section 874. First and second ends 876, 877 typically include inner portions 876*a* and 877*a* that extend inwardly toward the center of the attachment section 874. Post member 823 typically extends from the top side 878 of attachment section 874. In certain embodiments and similar to FIG. 43, the top side 878 may include a substantially planar section or region from which the post member 823 extends.

As noted above in connection with FIGS. 43-44 and 51, housing 714 typically includes at least one first groove or recess 767, and at least one second groove or recess 768 (FIGS. 44 and 51). In general, first groove 767 is configured and dimensioned to allow at least a portion of the first end 876 (e.g., inner portion 876*a*) of the attachment section 874 to be releasably positioned within at least a portion of first groove 767, and second groove 768 is configured and dimensioned to allow at least a portion of the second end 877 (e.g., inner portion 877*a*) of the attachment section 874 to be releasably positioned within at least a portion of second groove 768, in order to releasably secure or attach the receiver member 817 to housing 714 (e.g., similar to FIG. 44).

In exemplary embodiments, the first and second ends 876, 877 of the attachment section 874 are configured and dimensioned to flex, bend or expand outwardly when the attachment section 874 is positioned around the housing 714 until at least a portion of first and second ends 876, 877 are positioned within first and second grooves 767, 768, respectively, to releasably secure/attach the attachment section 874 to housing 714 (e.g., in a snap-on or clip-on fashion or manner). In short, attachment section 874 is configured to releasably clip-on or snap on to housing 714, with ends 876, 877 flexing outwardly over housing 714 until the ends are positioned within grooves 767, 768, respectively. In this manner, attachment section 874 may be releasably secured or attached to housing 714. Thereafter and as previously noted with respect to receiver member 717, receiver member 817 is similarly configured and dimensioned to be releasably secured or attached to a user-operable surgical device 719 (or device 319, etc.).

Similar to receiver member 717 (and receiver member 517 above), the post member 823 of receiver member 817 has a first end 827 and a second end 829, with the first end 827 typically being wider (e.g., laterally wider) than the second end 829 (e.g., the post member 823 tapers from the first end 827 to the second end 829).

In exemplary embodiments, the user-operable grasper member 719 (or 319, etc.) includes first and second end effectors 737, 739. Each end effector 737, 739 may or may not include slots. As such, a user may operate the user-operable grasper member 719 (or device 319), either manually or tele-surgically, to open or widen the first and second end effectors 737, 739, and then to position the first and second end effectors 737, 739 adjacent to the left side and right sides of post member 823, respectively. The user may then operate the device 719 to then close the end effectors 737, 739 so that at least a portion of the left side of post member 823 is releasably secured to end effector 737, and at least a portion of the right side of post member 823 is releasably secured to end effector 739 (similar to FIG. 30). In this releasably secured position, at least a portion of end effectors 737, 739 are positioned against at least a portion of post member 823.

In this way, user-operable surgical device 719 is now releasably secured or attached to receiver member 817, and a user may then move/position the receiver member 817 attached to housing 714 to any desired position and/or location (e.g., for imaging/surgical purposes) by operating device 719 (e.g., either manually or tele-surgically).

It is to be noted that prior to releasably securing device 719 to receiver member 817, the device 719 may approach receiver member 817 from a variety of angles/positions. For example and as similarly shown in FIGS. 27, 28 and 30, the device 719 (or device 319) may approach receiver member 817 from the proximal end of housing 714. Alternatively and as similarly shown in FIG. 29, device 719 may approach receiver member 817 from a different position (e.g., from a position located above the receiver member 817) so that at least a portion of end effectors 737, 739 are positioned against at least a portion of post member 823 once device 719 is releasably secured to receiver member 817. Similar to the embodiment as depicted in FIGS. 37 and 37A, receiver member 817 may includes a post member 823 that is slightly tapered from the bottom side to the top side to facilitate the releasable securement of device 719 to receiver member 817 from a variety of angles/positions (e.g., from a position located above the receiver member 817 as shown in FIG. 29).

As previously noted, the first end 827 of the post member 823 is typically wider than the second end 829 of the post member 823, and this structural feature/configuration of receiver member 817 further ensures that surgical device 719 is appropriately releasably secured or attached to receiver member 817.

It is to be noted that post member 823 of receiver member 817 may include at least one projection or protrusion that is configured and dimensioned to operate in a structurally and functionally similar fashion to projections or protrusions 537c, 539c, 537d or 539d as disclosed and described above in conjunction with FIGS. 34-35 and FIGS. 38-39.

Furthermore and as shown in FIGS. 55-56, it is also to be noted that post member 823a or 823b of receiver member 817a or 817b may include at least one surface (surfaces 837a and 839a in FIG. 56, and surfaces 837b and 839b in FIG. 55) that is configured and dimensioned to operate in a structurally and functionally similar fashion to surfaces 537a, 539a, 537b or 539b, respectively, as disclosed and described above in conjunction with FIGS. 32-33 and FIGS. 36-36A.

Figure 57:
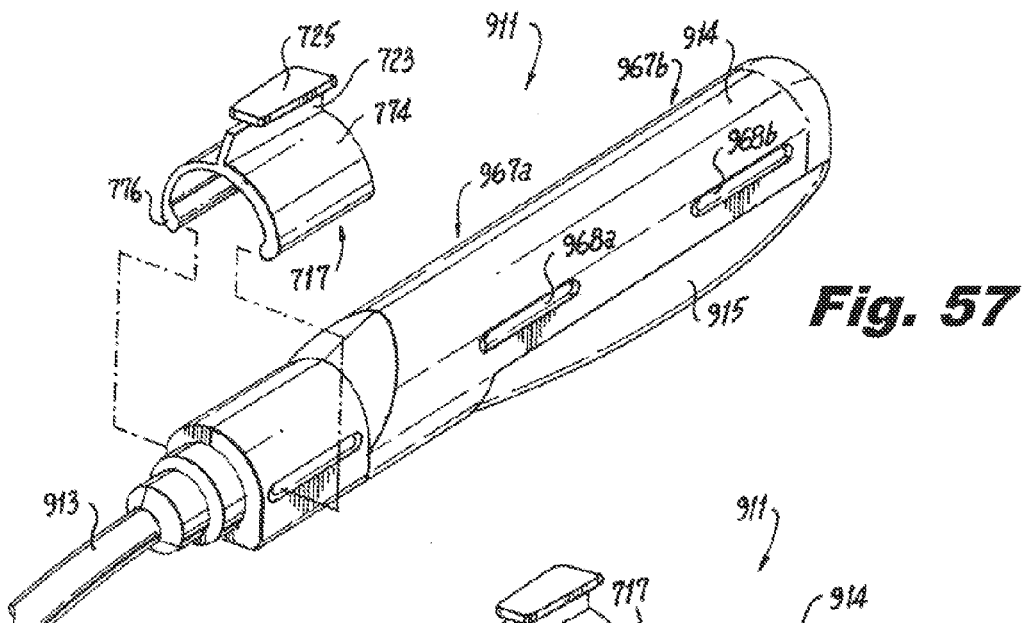
FIGS. 57-59 are side perspective views of another exemplary assembly for use in a surgical procedure, prior to attachment of the receiver member.
Figure 58:
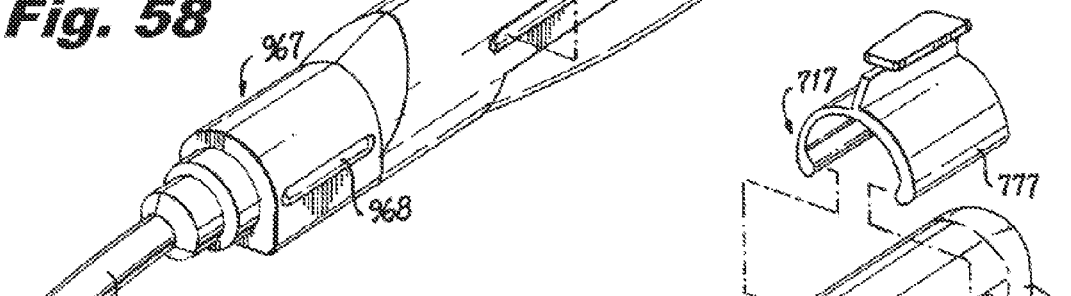

Turning now to FIGS. 57-59, an alternative assembly 911 may be utilized in conjunction with a user-operable surgical device 719 (or device 19, or device 219, etc.). Assembly 911 may be structurally and functionally similar to the assembly 11 and/or assembly 711 discussed above, with some differences.

Similar to assembly 11, the assembly 911 for use in a surgical procedure is typically attached or mounted with respect to a flexible cable 913 or the like. Exemplary assembly 911 takes the form of an imaging assembly (e.g., an ultrasound imaging assembly), although the present disclosure is not limited thereto. Rather, assembly 911 may take a variety of forms to allow a surgeon or technician to extend at least a portion of the assembly 911 to a surgical site for imaging and/or surgical purposes, as discussed above in conjunction with assembly 11.

As shown in FIGS. 57-59, exemplary assembly 911 typically includes housing 914, imaging member 915, and receiver member 717 (or 817). As noted above, receiver member 717 is typically configured and dimensioned to be releasably secured or attached to a user-operable surgical device 719. As such, a user may then manipulate the user-operable surgical device 719 to thereby move/position the releasably secured assembly 911 to any desired position and/or location.

Similar to the releasable attachment of receiver member 717 to housing 714 (FIG. 43), receiver member 717 (or receiver member 817, etc.) may be releasably secured or attached to housing 914. In exemplary embodiments and as shown in FIGS. 57-59, housing 914 includes first grooves 967, 967a and 967b (obscured), and second grooves 968, 968a and 968b.

In general, first grooves 967, 967a and 967b are each configured and dimensioned to allow at least a portion of the first end 776 (e.g., inner portion 776a) of the attachment section 774 to be releasably positioned within at least a portion of each first groove 967, 967a and 967b, and second grooves 968, 968a and 968b are each configured and dimensioned to allow at least a portion of the second end 777 (e.g., inner portion 777a) of the attachment section 774 to be releasably positioned within at least a portion of each second groove 968, 968a and 968b, in order to releasably secure or attach the receiver member 717 to housing 914 (FIGS. 57-59). Stated another way, to releasably secure the receiver member 717 to the proximal portion of housing 914, first end 776 would be positioned within first groove 967, and second end 777 would be positioned within second groove 968 (FIG. 57). Similarly, to releasably secure the receiver member 717 to the central portion of housing 914, first end 776 would be positioned within first groove 967a, and second end 777 would be positioned within second groove 968a (FIG. 58). Additionally, to releasably secure the receiver member 717 to the distal portion of housing 914, first end 776 would be positioned within first groove 967b, and second end 777 would be positioned within second groove 968b (FIG. 59). It is noted that housing 914 (or 14, or 714, etc.) may include any number of grooves to allow the receiver member 717 (or 817) to be positioned at a variety of locations along housing 914.

As similarly described above in connection with FIG. 44, the first and second ends 776, 777 of the attachment section 774 are configured and dimensioned to flex, bend or expand outwardly when the attachment section 774 is positioned around the housing 914 until at least a portion of first and second ends 776, 777 are positioned within first and second grooves 967, 968 (or grooves 967a, 968a—or grooves 967b, 968b), respectively, to releasably secure/attach the attachment section 774 to housing 914 (e.g., in a snap-on or clip-on fashion or manner). In short, attachment section 774 is configured to releasably clip-on or snap on to housing 914, with ends 776, 777 flexing outwardly over housing 914 until the ends are positioned within grooves 967, 968, respectively. In this manner, attachment section 774 may be releasably secured or attached to housing 914 of assembly 911. Thereafter and as noted, receiver member 717 is typically configured and dimensioned to be releasably secured or attached to a user-operable surgical device 719. As such, a user may then manipulate the user-operable surgical device 719 to thereby move/position the releasably secured assembly 911 to any desired position and/or location (e.g., in a minimally invasive manner within the surgical site for imaging, surgical and/or diagnostic purposes).

Although the systems, assemblies and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. An assembly for use in a surgical procedure comprising:
 a housing defining a top side, a bottom side, a left side and a right side, with a first groove positioned in the left side of the housing and a second groove positioned in the right side of the housing;
 an imaging member mounted to the bottom side of the housing;
 a U-shaped or C-shaped attachment member extending from a first end to a second end to define the U-shaped or C-shaped attachment member, with a post member extending from the attachment member and a securing member extending past both sides of the post member to define a fin-shaped portion extending from the attachment member;

wherein the first end of the U-shaped or C-shaped attachment section member is configured and dimensioned to be releasably positioned within the first groove of the housing, and the second end of the U-shaped or C-shaped attachment member is configured and dimensioned to be releasably positioned within the second groove of the housing to releasably secure the U-shaped or C-shaped attachment member to the top side, left side and right side of the housing in a first position;

wherein the fin-shaped portion extending from the attachment member is configured and dimensioned to be releasably secured to a user-operable surgical device; and wherein the housing and the releasably secured U-shaped or C-shaped attachment member are configured and dimensioned to be inserted into a patient and moved to a surgical site within the patient by the user-operable surgical device.

2. The assembly of claim 1 wherein the imaging member is an ultrasound transducer.

3. The assembly of claim 2, wherein the housing is mounted with respect to a flexible cable; and wherein the imaging member is configured and dimensioned to capture an image of a surgical site.

4. The assembly of claim 1, wherein the user-operable surgical device includes first and second end effectors, the first end effector having a first slit and the second end effector having a second slit;

wherein the securing member has a first side and a second side; and wherein at least a portion of the first side of the securing member extends through the first slit and at least a portion of the second side of the securing member extends through the second slit when the user-operable surgical device is releasably secured to the U-shaped or C-shaped attachment member.

5. The assembly of claim 1, wherein the securing member has a first end and a second end and the post member defines a longitudinal axis; and wherein the securing member tapers from the first end to the second end with the first end of the securing member extending a greater distance from the longitudinal axis relative to the distance that the second end of the securing member extends from the longitudinal axis.

6. The assembly of claim 1, wherein the post member has a first end and a second end, the post member tapering from the first end to the second end with the first end being wider than the second end.

7. The assembly of claim 1, wherein the user-operable surgical device is a minimally invasive user-operable surgical device; and wherein the housing and the releasably secured U-shaped or C shaped attachment member are configured and dimensioned to be: (i) inserted through a guide tool located in a minimally invasive incision of the patient, and (ii) moved to the surgical site within the patient by the minimally invasive user-operable surgical device.

8. The assembly of claim 1, wherein the user-operable surgical device includes first and second end effectors;

wherein the post member has a first side and a second side; and wherein when the user-operable surgical device is releasably secured to the U-shaped or C-shaped attachment member, at least a portion of the first side of the post member is adjacent to at least a portion of the first end effector, at least a portion of the second side of the post member is adjacent to at least a portion of the second end effector, and at least a portion of the first and second end effectors are positioned underneath the securing member.

9. The assembly of claim 1, wherein the post member has a first side and a second side, the first and second sides each having a grooved or textured surface.

10. The assembly of claim 1, wherein the post member has a first side and a second side, the first and second sides each having a protrusion or extending member;

wherein the user-operable surgical device includes first and second end effectors, the first and second end effectors each having a recess or concave portion; and wherein when the user-operable surgical device is releasably secured to the U-shaped or C-shaped attachment member, at least a portion of the protrusion or extending member of the first side of the post member is positioned within at least a portion of the recess or concave portion of the first end effector, and at least a portion of the protrusion or extending member of the second side of the post member is positioned within at least a portion of the recess or concave portion of the second end effector.

11. The assembly of claim 1, wherein the first end of the attachment member includes an inner portion that extends inwardly toward the center of the attachment member, and the second end of the attachment member includes an inner portion that extends inwardly toward the center of the attachment member.

12. The assembly of claim 1, wherein the first and second ends of the attachment member flex outwardly when the attachment member is positioned around the housing to releasably secure the U-shaped or C shaped attachment member to the housing.

13. The assembly of claim 1, wherein the attachment member includes a hinge that facilitates the first and second ends of the attachment member to flex outwardly when the U-shaped or C-shaped attachment member is positioned around the housing.

14. The assembly of claim 1, wherein the attachment member includes a top side having a planar region; and wherein the post member extends from the planar region of the top side of the attachment member.

15. The assembly of claim 1, wherein the housing includes a proximal portion, a central portion and a distal portion, with the first and second grooves located on the proximal portion of the housing;

wherein the housing further comprises a third groove positioned in the left side of the housing and a fourth groove positioned in the right side of the housing, with the third and fourth grooves located on the central portion of the housing; and wherein of the first end of the attachment member is configured and dimensioned to be releasably positioned within the third groove of the housing, and the second end of the attachment member is configured and dimensioned to be releasably positioned within the fourth groove of the housing to releasably secure the U-shaped or C-shaped attachment member to the top side, left side and right side of the housing in a second position on the central portion of the housing.

16. The assembly of claim 15, wherein the housing further comprises a fifth groove positioned in the left side of the housing and a sixth groove positioned in the right side of the housing, with the fifth and sixth grooves located on the distal portion of the housing; and wherein the first end of the attachment member is configured and dimensioned to be releasably positioned within the fifth groove of the housing, and the second end of the attachment member is configured and dimensioned to be releasably positioned within the sixth groove of the housing to releasably secure the U-shaped or C-shaped attachment member to the top side, left side and right side of the housing in a third position on the distal portion of the housing.

17. An assembly for use in a surgical procedure comprising:
a housing defining a top side, a bottom side, a left side and a right side, with a first groove positioned in the left side of the housing and a second groove positioned in the right side of the housing;
an imaging member mounted to the bottom side of the housing;
a U-shaped or C-shaped attachment member extending from a first end to a second end to define the U-shaped or C-shaped attachment member, with a post member extending from the attachment member;
wherein the post member has a first end and a second end, the post member tapering from the first end to the second end with the first end being wider than the second end;
wherein the first end of the U-shaped or C-shaped attachment member is configured and dimensioned to be releasably positioned within the first groove of the housing, and the second end of the U-shaped or C-shaped attachment member is configured and dimensioned to be releasably positioned within the second groove of the housing to releasably secure the U-shaped or C-shaped attachment member to the top side, left side and right side of the housing in a first position;
wherein the tapered post member extending from the attachment member is configured and dimensioned to be releasably secured to a user-operable surgical device; and
wherein the housing and the releasably secured U-shaped or C-shaped attachment member are configured and dimensioned to be inserted into a patient and moved to a surgical site within the patient by the user-operable surgical device.

18. The assembly of claim 17 wherein the imaging member is an ultrasound transducer.

19. The assembly of claim 18, wherein the housing is mounted with respect to a flexible cable;
wherein the user-operable surgical device is a minimally invasive user-operable surgical device;
wherein the housing and the releasably secured U-shaped or C shaped attachment member are configured and dimensioned to be: (i) inserted through a guide tool located in a minimally invasive incision of a patient, and (ii) moved to a surgical site within the patient by the minimally invasive user-operable surgical device; and
wherein the imaging member is configured and dimensioned to capture an image of the surgical site.

20. The assembly of claim 17, wherein the user-operable surgical device includes first and second end effectors;
wherein the post member has a first side and a second side; and
wherein when the user-operable surgical device is releasably secured to the U-shaped or C-shaped attachment member, at least a portion of the first side of the post member is adjacent to at least a portion of the first end effector, and at least a portion of the second side of the post member is adjacent to at least a portion of the second end effector.

21. The assembly of claim 17, wherein the post member has a top side and a bottom side, the post member tapering from the bottom side to the top side with the bottom side being wider than the top side.

22. The assembly of claim 17, wherein the post member has a first side and a second side, the first and second sides each having a grooved or textured surface.

23. The assembly of claim 17, wherein the post member has a first side and a second side, the first and second sides each having a protrusion or extending member;
wherein the user-operable surgical device includes first and second end effectors, the first and second end effectors each having a recess or concave portion; and
wherein when the user-operable surgical device is releasably secured to the U-shaped or C-shaped attachment member, at least a portion of the protrusion or extending member of the first side of the post member is positioned within at least a portion of the recess or concave portion of the first end effector, and at least a portion of the protrusion or extending member of the second side of the post member is positioned within at least a portion of the recess or concave portion of the second end effector.

24. The assembly of claim 17, wherein the first end of the attachment member includes an inner portion that extends inwardly toward the center of the attachment member, and the second end of the attachment member includes an inner portion that extends inwardly toward the center of the attachment member.

25. The assembly of claim 17, wherein the first and second ends of the attachment member flex outwardly when the attachment member is positioned around the housing to releasably secure the U-shaped or C shaped attachment member to the housing.

26. The assembly of claim 17, wherein the attachment member includes a hinge that facilitates the first and second ends of the attachment member to flex outwardly when the U-shaped or C-shaped attachment member is positioned around the housing.

27. The assembly of claim 17, wherein the attachment member includes a top side having a substantially planar region; and
wherein the post member extends from the planar region of the top side of the attachment member.

28. The assembly of claim 17, wherein the housing includes a proximal portion, a central portion and a distal portion, with the first and second grooves located on the proximal portion of the housing;
wherein the housing further comprises a third groove positioned in the left side of the housing and a fourth groove positioned in the right side of the housing, with the third and fourth grooves located on the central portion of the housing; and
wherein the first end of the attachment member is configured and dimensioned to be releasably positioned within the third groove of the housing, and the second end of the attachment member is configured and dimensioned to be releasably positioned within the fourth groove of the housing to releasably secure the U-shaped or C-shaped attachment member to the top side, left side and right side of the housing in a second position on the central portion of the housing.

29. The assembly of claim 28, wherein the housing further comprises a fifth groove positioned in the left side of the housing and a sixth groove positioned in the right side of the housing, with the fifth and sixth grooves located on the distal portion of the housing; and wherein the first end of the attachment member is configured and dimensioned to be releasably positioned within the fifth groove of the housing, and the second end of the attachment member is configured and dimensioned to be releasably positioned within the sixth groove of the housing to releasably secure the U-shaped or C-shaped attachment member to the top side, left side and right side of the housing in a third position on the distal portion of the housing.

30. An imaging assembly comprising:

a housing defining a top side, a bottom side, a left side and a right side and including a proximal portion, a central portion and a distal portion, with a first groove positioned in the left side of the housing and located on the proximal portion of the housing, and with a second groove positioned in the right side of the housing and located on the proximal portion of the housing, and with a third groove positioned in the left side of the housing and located on the central portion of the housing, and with a fourth groove positioned in the right side of the housing and located on the central portion of the housing, and with a fifth groove positioned in the left side of the housing and located on the distal portion of the housing, and with a sixth groove positioned in the right side of the housing and located on the distal portion of the housing;

an imaging member mounted to the bottom side of the housing;

a U-shaped or C-shaped attachment member extending from a first end to a second end to define the U-shaped or C-shaped attachment member, with a post member extending from the attachment member and a securing member extending past both sides of the post member to define a fin-shaped portion extending from the attachment member;

wherein the first end of the attachment member includes an inner portion that extends inwardly toward the center of the attachment member, and the second end of the attachment member includes an inner portion that extends inwardly toward the center of the attachment member;

wherein the inner portion of the first end of the attachment member is configured and dimensioned to be releasably positioned within the first groove of the housing, and the inner portion of the second end of the attachment member is configured and dimensioned to be releasably positioned within the second groove of the housing to releasably secure the U-shaped or C-shaped attachment member to the top side, left side and right side of the housing in a first position on the proximal portion of the housing;

wherein the inner portion of the first end of the attachment member is configured and dimensioned to be releasably positioned within the third groove of the housing, and the inner portion of the second end of the attachment member is configured and dimensioned to be releasably positioned within the fourth groove of the housing to releasably secure the U-shaped or C-shaped attachment member to the top side, left side and right side of the housing in a second position on the central portion of the housing;

wherein the inner portion of the first end of the attachment member is configured and dimensioned to be releasably positioned within the fifth groove of the housing, and the inner portion of the second end of the attachment member is configured and dimensioned to be releasably positioned within the sixth groove of the housing to releasably secure the U-shaped or C-shaped attachment member to the top side, left side and right side of the housing in a third position on the distal portion of the housing;

wherein the fin-shaped portion extending from the attachment member is configured and dimensioned to be releasably secured to a user-operable surgical device; and wherein the housing is and the releasably secured U-shaped or C-shaped attachment member are configured and dimensioned to be inserted into a patient and moved to a surgical site within the patient by the user-operable surgical device, the releasably secured U-shaped or C-shaped attachment member in the first position, the second position or the third position.

* * * * *